(12) United States Patent
El-Nezamy et al.

(10) Patent No.: US 10,016,468 B2
(45) Date of Patent: Jul. 10, 2018

(54) METHOD AND COMPOSITIONS FOR TREATING CANCER USING PROBIOTICS

(71) Applicant: THE UNIVERSITY OF HONG KONG, Hong Kong (CN)

(72) Inventors: Hani El-Nezamy, Hong Kong (CN); Nikki Pui-Yue Lee, Hong Kong (CN); Cecilia Ying Ju Sung, Hong Kong (CN); Jiandong Huang, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 0 days.

(21) Appl. No.: 14/460,732

(22) Filed: Aug. 15, 2014

(65) Prior Publication Data
US 2015/0164964 A1 Jun. 18, 2015

Related U.S. Application Data

(60) Provisional application No. 61/866,784, filed on Aug. 16, 2013.

(51) Int. Cl.
*A61K 35/741* (2015.01)
*A61K 35/744* (2015.01)
*A61K 35/745* (2015.01)
*A61K 35/747* (2015.01)
*A61K 35/00* (2006.01)

(52) U.S. Cl.
CPC .......... *A61K 35/741* (2013.01); *A61K 35/744* (2013.01); *A61K 35/745* (2013.01); *A61K 35/747* (2013.01); *A61K 2035/115* (2013.01)

(58) Field of Classification Search
None
See application file for complete search history.

(56) References Cited

PUBLICATIONS

Yeo, et al. Journal of the National Cancer Institute, 2005, vol. 97, No. 20, p. 1532-1538.*
Choi et al., Letters in Applied Microbiology, 2006, vol. 42, p. 452-458.*
Stritzker et al., International Journal of Medical Microbiology, 2007, vol. 297, p. 151-162.*
Ouwehand et al., Letters in Applied Microbiology, 2000, vol. 31, p. 82-86.*
Lactobacillus rhamnosus ATCC 53103 product information page, downloaded from www.atcc.org/products/all/53103.aspx#generalinformation on Apr. 27, 2016.*
Schlee et al., Clinical and Experimental Immunology, 2007, vol. 151, p. 528-535.*
Appleyard et al., Am J Physiol Gastrointest Liver, 2011, vol. 301, p. G1004-G10012.*
Soff, G., Hepatology, 2003, p. 505-506 "Editorials".*
Lata et al., Eur J Gastroenterol Hepatol., 2007, vol. 19, No. 1, p. 1111-1113, Abstract Only.*
Bruix et al., Hepatology, 2005, vol. 42, No. 5, p. 1208-1236.*
Ferlay, Jacques, et al., Estimates of worldwide burden of cancer in 2008: GLOBOCAN 2008, International Journal of Cancer, 2010, 127(12):2893-2917, UICC.
El-Serag, Hashem B., et al., Hepatocellular Carcinoma: Epidemiology and Molecular Carcinogenesis, Gastroenterology, 2007, 132(7):2557-2576, AGA Institute.
Venook, Alan P., et al., The Incidence and Epidemiology of Hepatocellular Carcinoma: A Global and Regional Perspective, The Oncologist, 2010, 15 (Supplement 4):5-13, AlphaMed Press.
De Leblanc, Alejandra De Moreno, et al., The application of probiotics in cancer, British Journal of Nutrition, 2007, 98(Supplement 1):S105-S110.
Perdigon, G., et al., Role of yoghurt in the prevention of colon cancer, European Journal of Clinical Nutrition, 2002, 56(Supplement 3):S65-S68, Nature Publishing Group.
De Leblanc, Alejandra De Moreno, et al., Effects of milk fermented by *Lactobacillus helveticus* R389 on immune cells associated to mammary glands in normal and a breast cancer model, Immunobiology, 2005, 210(5): 349-358, Elsevier GmbH.
El-Nezami, Hani S., et al., Probiotic supplementation reduces a biomarker for increased risk of liver cancer in young men from Southern China, the American journal of clinical nutrition, 2006, 83(5):1199-1203, American Society for Nutrition, USA.
Braat, Henri, etal., *Lactobacillus rhamnosus* induces peripheral hyporesponsiveness in stimulated $CD4^{1+}$ T cells via modulation of dendritic cell function, The American Journal of Clinical Nutrition, 2004, 80(6):1618-1625, American Society for Clinical Nutrition, USA.
Saxelin, Maija, LGG® Summatim: Lactobacillus GG and its health effects, Second, updated edition, in Health effects of LGG2009, 2002, 1-59, Valio Ltd, R&D, Helsinki, Finland.
Appleyard, Caroline B., et al., Pretreatment with the probiotic VSL# 3 delays transition from inflammation to dysplasia in a rat model of colitis-associated cancer, American Journal of Physiology—Gastrointestinal and Liver Physiology, 2011, 301(6):G1004-G1013, American Physiological Society.
Sashihara, T., et al., An Analysis of the Effectiveness of Heat-Killed Lactic Acid Bacteria in Alleviating Allergic Diseases, Journal of Dairy Science, 2006, 89(8):2846-2855, American Dairy Science Association.
Hoption Cann, S. A., et al., Dr William Coley and tumour regression: a place in history or in the future, Postgraduate Medical Journal, 2003, 79(938):672-680.
Richardson, Mary Ann, et al., Coley Toxins Immunotherapy: A Retrospective Review, Alternative Therapies in Health and Medicine, May 1999, 5(3):42-47.

(Continued)

*Primary Examiner* — Kade Ariani
(74) *Attorney, Agent, or Firm* — Saliwanchik, Lloyd & Eisenschenk

(57) ABSTRACT

The subject invention pertains to probiotic compositions and methods of treating hepatocellular carcinoma (HCC) using the probiotic compositions. The probiotic compositions can inhibit growth of HCC. The probiotic compositions can reduce the risk of HCC. The probiotic compositions include a specific combination of three bacterial compositions: (a) heat-inactivated *Lactobacillus rhamnosus* GG deposited under accession number ATCC 53103, also known as, *Lactobacillus acidophilus* (Moro) Hansen and Macquot, (b) viable *Escherichia coli* Nissle 1917, and (c) heat-inactivated VSL#3®. This combination of bacteria is effective to reduce hepatocellular carcinoma (HCC) growth compared to control growth.

14 Claims, 30 Drawing Sheets

(56) References Cited

PUBLICATIONS

Cabrera, R., et al., Review article: the management of hepatocellular carcinoma, Alimentary Pharmacology & Therapeutics, 2010, 31(4):461-476, Blackwell Publishing Ltd.

Benson III, Al B., et al., Hepatobiliary Cancers: Clinical Practice Guidelines in Oncology™, Journal of the National Comprehensive Cancer Network, Apr. 2009, 7(4):350-391.

Jelic, S., Hepatocellular carcinoma: ESMO Clinical Recommendations for diagnosis, treatment and follow-up, Annals of Oncology, 2009, 20(Supplement 4):iv41-iv45, Oxford University Press on behalf of the European Society for Medical Oncology.

Izumi, Namiki, Diagnostic and Treatment Algorithm of the Japanese Society of Hepatology: A Consensus-Based Practice Guideline, Oncology, 2010, 78(Supplement 1):78-86, S. Karger AG, Basel.

Bruix, Jordi, et al., Management of Hepatocellular Carcinoma: An Update, Hepatology, 2011, 53(3):1020-1022, American Association for the Study of Liver Diseases.

Yabroff, K. Robin, et al., Cost of Care for Elderly Cancer Patients in the United States, Journal of the National Cancer Institute, 2008, 100(9):630-641, Oxford University Press.

Block, Timothy M., et al., Molecular viral oncology of hepatocellular carcinoma, Oncogene, 2003, 22(33):5093-5107, Nature Publishing Group.

Anthony, P. P., Hepatocellular carcinoma: an overview, Histopathology, 2001, 39(2):109-118, Blackwell Science Limited.

Sung, Cecilia Ping Ju, et al., Regulation of T helper 17 by Bacteria: An Approach for the Treatment of Hepatocellular Carcinoma, International Journal of Hepatology, 2012, 2012(Article ID 439024):1-8, Hindawi Publishing Corporation.

Haskard, Carolyn A., et al., Surface Binding of Aflatoxin B1 by Lactic Acid Bacteria, Applied and Environmental Microbiology, Jul. 2001, 67(7):3086-3091, American Society for Microbiology.

El-Nezami, H., et al., Ability of Dairy Strains of Lactic Acid Bacteria to Bind a Common Food Carcinogen, Aflatoxin $B_1$, Food and Chemical Toxicology, 1998, 36:321-326, Elsevier Science Ltd., Great Britain.

Zhao, Gui-Jun, et al., Establishment of an orthotopic transplantation tumor model of hepatocellular carcinoma in mice, World Journal of Gastroenterology, Dec. 21, 2012, 18(47):7087-7092, Baishideng.

Choi, S. S., et al., Effects of *Lactobacillus* strains on cancer cell proliferation and oxidative stress in vitro, Letters in Applied Microbiology, 2006, 42:452-458, The Society for Applied Microbiology.

Stritzker, Jochen, et al., Tumor-specific colonization, tissue distribution, and gene induction by probiotic *Escherichia coil* Nissle 1917 in live mice, International Journal of Medical Microbiology, 2007, 297:151-162, Elsevier GmbH.

\* cited by examiner

METHOD AND COMPOSITIONS FOR TREATING CANCER USING PROBIOTICS

CROSS-REFERENCE TO RELATED APPLICATION

This application claims the benefit of U.S. provisional application Ser. No. 61/866,784, filed Aug. 16, 2013, which is herein incorporated by reference in its entirety.

BACKGROUND OF THE INVENTION

Hepatocellular carcinoma (HCC) is the fifth most prevalent cancer and the third leading cause of all cancer-related deaths in the world (Ferlay, J., et al., *Estimates of worldwide burden of cancer in 2008: GLOBOCAN 2008*. International journal of cancer, 2010. 127(12): p. 2893-2917). More than 600,000 deaths are reported globally each year. HCC affects all segments of the world population (El-Serag, H. B. and K. L. Rudolph, *Hepatocellular carcinoma: epidemiology and molecular carcinogenesis*. Gastroenterology, 2007. 132(7): p. 2557-2576). Approximately 75% of HCC patients are concentrated in Asia, but a recent trend of rising rates of HCC has been reported in several developed countries including Europe and the United States (Venook, A. P., et al., *The incidence and epidemiology of hepatocellular carcinoma: a global and regional perspective*. The Oncologist, 2010. 15 (Supplement 4): p. 5-13).

The current standard of care can be classified into 3 broad categories including (1) surgical treatment; (2) local ablation therapy; and (3) chemotherapy. Surgical treatments include hepatic resection and liver transplantation. Non-surgical treatments include local ablation therapies, of which percutaneous ethanol injection (PEI) and radiofrequency ablation (RFA) are most commonly practiced; and chemotherapy which is either administered via transarterial chemoembolization (TACE) or systemically. Standard treatments involve high costs. For example, molecular targeted therapy using sorafenib as recommended by NCCN/AASLD/JSH/ESMO Guideline is expensive, with an average cost around US$6,000 per month.

Oral consumption of viable probiotics is one of the many alternative experimental cancer treatments that have been reported in the literature. Probiotics are defined as live microorganisms that, when administered in adequate amounts, confer a health benefit on the host. Efficacy of probiotics on cancer development is suggested by several lines of scientific evidence and hypotheses, including the increase in immune cell activation, increase of the antitumor surveillance immune activity, promotion of anti-inflammation, and the suppression of bacteria converting procarcinogens (de LeBlanc, A. d. M., C. Matar, and G. Perdigón, *The application of probiotics in cancer*. British Journal of Nutrition, 2007. 98(S1): p. 5105-5110). Most data were obtained from cases of colon and breast carcinomas. In the former, prevention was first achieved in animal models and was ascribed to the significant anti-inflammatory effect of probiotics (Perdigon, G., et al., *Role of yoghurt in the prevention of colon cancer*. European journal of clinical nutrition, 2002. 56: p. S65). While in the case of breast cancer, suggested beneficial effects of probiotics appear to be mediated by an increase of the antitumor surveillance immune activity (de Moreno de LeBlanc, A., et al., *Effects of milk fermented by Lactobacillus helveticus R389 on immune cells associated to mammary glands in normal and a breast cancer model*. Immunobiology, 2005. 210(5): p. 349-358).

In the context of liver cancer, there are reports regarding the use of probiotic supplement (viable *Lactobacillus rhamnosus* LC705 and *Propionibacterium freudenreichii* subsp. *Shermani*) as a dietary approach to decrease the risk of liver cancer. The proposed mechanism is related to blocking intestinal absorption of carcinogen aflatoxin B1 by binding to the aflotoxin, and thereby reducing the biologically effective dose of dietary aflatoxin exposure (El-Nezami, H. S., et al., *Probiotic supplementation reduces a biomarker for increased risk of liver cancer in young men from Southern China*. The American journal of clinical nutrition, 2006. 83(5): p. 1199-1203).

There is substantial evidence that some probiotics can provide benefits by modulating immune functions, including modulating T helper cell response. Depending on the disease model, these probiotics may induce T-cell hyporesponsiveness (Braat, H., et al., *Lactobacillus rhamnosus induces peripheral hyporesponsiveness in stimulated CD4+ T cells via modulation of dendritic cell function*. The American journal of clinical nutrition, 2004. 80(6): p. 1618-1625), up-regulating or down-regulating production of cytokines relating to Th1/Th2 response (Valio Ltd, R.D.a.S., *LGG® Summatim*, in *Health effects of LGG*2009; Mutaflor. *Most Recent Mutaflor Evidence and Clinical Studies* (2006-2010). 2010; Available on webpagemutaflor.ca/health-care-professionals/mutaflor-clinical-studies/; Sigma-Tau Pharmaceuticals, I. *VSL#3® references*. 2012; Available on webpage vsl3.com/hcp/references.asp). *Escherichia coli* Nissle 1917 (EcN) has been clinically studied for use in ulcerative colitis, Crohn's Disease, chronic constipation, prolonged diarrhea, irritable bowel syndrome and pouchitis (Mutaflor. *Most Recent Mutaflor Evidence and Clinical Studies* (2006-2010). 2010; Available on webpagemutaflor.ca/health-care-professionals/mutaflor-clinical-studies/). *Lactobacillus acidophilus* (Moro) Hansen and Mocquot strain GG (ATCC 53103) (LGG) has been shown to enhance antibody formation during viral infection and respiratory infections, in addition to treating the above gastrointestinal disorder (Valio Ltd, R.D.a.S., *LGG® Summatim*, in *Health effects of LGG*2009). VSL#3® (Sigma-Tau) is also widely used in clinical management of ulcerative colitis, irritable bowel syndrome, and ileal pouch (Sigma-Tau Pharmaceuticals, I. *VSL#3® references*. 2012; Available on webpage vsl3.com/hcp/references.asp). In animal models, VSL#3® has shown protective efficacy in delaying transition to dysplasia in colitis-associated colorectal by attenuating various inflammatory-associated parameters (Appleyard, C. B., et al., *Pretreatment with the probiotic VSL#3 delays transition from inflammation to dysplasia in a rat model of colitis-associated cancer*. American Journal of Physiology-Gastrointestinal and Liver Physiology, 2011. 301(6): p. G1004-G1013).

Apart from viable probiotics, health benefits of heat-inactivated probiotics supplementation have also been studied, although the disease model is not cancer. Probiotic strains such as *L. acidophilus* L-92, *L. brevis* SBC8803, *L. casei Shirota*, *L. gasseri* OLL2809, *L. paracasei* KW3110, *L. pentosus* S-PT84 still show immunomodulatory functions, including affecting IgE production, and affecting Th1/Th2 cytokine production even after heat treatment in animal models of sensitization and allergic manifestations (Sashihara, T., N. Sueki, and S. Ikegami, *An analysis of the effectiveness of heat-killed lactic acid bacteria in alleviating allergic diseases*. Journal of dairy science, 2006. 89(8): p. 2846-2855). Meanwhile, non-probiotic bacteria have been heat-attenuated and used in cancer studies in the form of cancer vaccines. Examples of this include Coley's toxins, a mixture of heat-killed *S. pyogenes* and *S. marcescens*, where attenuated bacteria have been administered systemically to induce severe inflammatory reaction against tumor by bacteria's endotoxin and induce apoptosis. Though it is mainly used in the treatment of sarcomas, lymphomas and melanomas (Cann, S. H., J. Van Netten, and C. Van Netten, *Dr William Coley and tumour regression: a place in history or in the future*. Postgraduate medical journal, 2003. 79(938): p. 672-680), its use in HCC patients has been reported in one study as an adjuvant treatment. However, this kind of treatment could be followed by severe fever with high risk of patient's death (Richardson, M. A., et al., *Coley toxins immunotherapy: a retrospective review*. Alternative therapies in health and medicine, 1999. 5(3): p. 42).

BRIEF SUMMARY OF THE INVENTION

It is an object of the present invention to provide probiotic compositions that can treat cancer by, for example, inhibiting the growth of the cancer. It is another object of the invention to provide methods of treating cancer with probiotic compositions.

It is desirable to prepare a probiotic formulation which would act as a food supplement and therapeutic agent that assist in reducing growth of hepatocellular carcinoma (HCC). To that end, the disclosed probiotic formulations are useful as a food supplement and therapeutic agent, and additionally are particularly useful for reducing HCC growth.

Aspects of the present invention provide probiotic compositions comprising an effective amount of a combination of bacteria, where the combination of bacteria comprises (a) heat-inactivated *Lactobacillus rhamnosus* GG deposited under accession number ATCC 53103, also known as, *Lactobacillus acidophilus* (Moro) Hansen and Macquot, (b) viable *Escherichia coli* Nissle 1917, and (c) heat-inactivated VSL#3®. The combination of bacteria can be effective to reduce hepatocellular carcinoma (HCC) growth compared to control growth. The bacteria (a), (b), and (c) can each independently be present in the probiotic composition at a concentration of about 20-55 weight percent.

VSL#3® comprises *Bifidobacterium breve, Bifidobacterium longum, Bifidobacterium infantis, Lactobacillus acidophilus, Lactobacillus plantarum, Lactobacillus paracasei, Lactobacillus bulgaricus* and *Streptococcus thermophiles*.

In at least one embodiment, the present invention provides probiotic compositions comprising an effective amount of a combination of bacteria, wherein the combination of bacteria comprises (a) heat-inactivated *Lactobacillus rhamnosus* GG deposited under accession number ATCC 53103, also known as, *Lactobacillus acidophilus* (Moro) Hansen and Macquot, (b) viable *Escherichia coli* Nissle 1917, and (c) heat-inactivated bacteria selected from the group consisting of *Bifidobacterium breve, Bifidobacterium longum, Bifidobacterium infantis, Lactobacillus acidophilus, Lactobacillus plantarum, Lactobacillus paracasei, Lactobacillus bulgaricus, Streptococcus thermophiles* and combinations thereof.

Aspects of the present invention also provide methods of treating hepatocellular carcinoma (HCC). The methods comprise orally administering a probiotic composition to a subject at risk of or diagnosed with HCC. The probiotic composition can be administered in any effective schedule. For example, and not meant to be limiting, the probiotic composition can be administered daily. The probiotic composition can be administered daily for at least one month. The subject can be diagnosed with HCC. The subject can be at risk of HCC. The subject can be a subject diagnosed with hepatitis B virus, hepatitis C virus, or both. The subject can be a subject exposed to aflatoxin B1 (AFB1). The subject can be a subject diagnosed with alcoholism.

The methods can further comprise, prior to administering the probiotic composition, diagnosing the subject as having HCC. The methods can further comprise, prior to administering the probiotic composition, diagnosing the subject as at risk of HCC. Diagnosing the subject as at risk of HCC can comprise diagnosing the subject as having hepatitis B virus, hepatitis C virus, or both. Diagnosing the subject as at risk of HCC can comprise diagnosing the subject as having been exposed to aflatoxin B1 (AFB1). Diagnosing the subject as at risk of HCC can comprise diagnosing the subject as having alcoholism.

Also disclosed are methods comprising diagnosing the subject as having or being at risk of HCC and orally administering a probiotic composition to the subject diagnosed as having or being at risk of HCC.

The probiotic composition can be any of the disclosed probiotic compositions. For example, and not meant to be limiting, the probiotic composition can comprise an effective amount of a combination of bacteria, where the combination of bacteria comprises (a) heat-inactivated *Lactobacillus rhamnosus* GG deposited under accession number ATCC 53103, also known as, *Lactobacillus acidophilus* (Moro) Hansen and Macquot, (b) viable *Escherichia coli* Nissle 1917, and (c) heat-inactivated bacteria selected from the group consisting of *Bifidobacterium breve, Bifidobacterium longum, Bifidobacterium infantis, Lactobacillus acidophilus, Lactobacillus plantarum, Lactobacillus paracasei, Lactobacillus bulgaricus, Streptococcus thermophiles* and combinations thereof. The combination of bacteria can be effective to reduce hepatocellular carcinoma (HCC) growth compared to control growth. The bacteria (a), (b), and (c) can each independently present in the probiotic composition at a concentration of about 20-55 weight percent.

In at least one embodiment, the present invention provides a method of treating a subject comprising orally administering a probiotic composition to a subject at risk of or diagnosed with hepatocellular carcinoma (HCC), the probiotic composition comprising an effective amount of a combination of bacteria, wherein the combination of bacteria comprises (a) heat-inactivated *Lactobacillus rhamnosus* GG deposited under accession number ATCC 53103, also known as, *Lactobacillus acidophilus* (Moro) Hansen and Macquot, (b) viable *Escherichia coli* Nissle 1917, and (c) heat-inactivated bacteria selected from the group consisting of *Bifidobacterium breve, Bifidobacterium longum, Bifidobacterium infantis, Lactobacillus acidophilus, Lactobacillus plantarum, Lactobacillus paracasei, Lactobacillus bulgaricus, Streptococcus thermophiles* and combinations thereof.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 9A shows RT-qPCR analysis of Tbet, Gata3, Roryt and Foxp3 mRNA expression. Expression is presented relative to Gapdh expression. FIG. 9B shows cytokine secretion measured by ELISA in supernatants of CD4+ T cells differentiated for 3 days. FIG. 9C shows flow cytometry analysis of % Th1(CD4+IFN-γ+), Th2 (CD4+IL-4+) and Th17 (CD4+IL-17+) derived from naïve CD4+ T cells under polarizing conditions assessed for 5 day culture. Representative data from three independent experiments are shown.

DETAILED DISCLOSURE OF THE INVENTION

Figure 1:
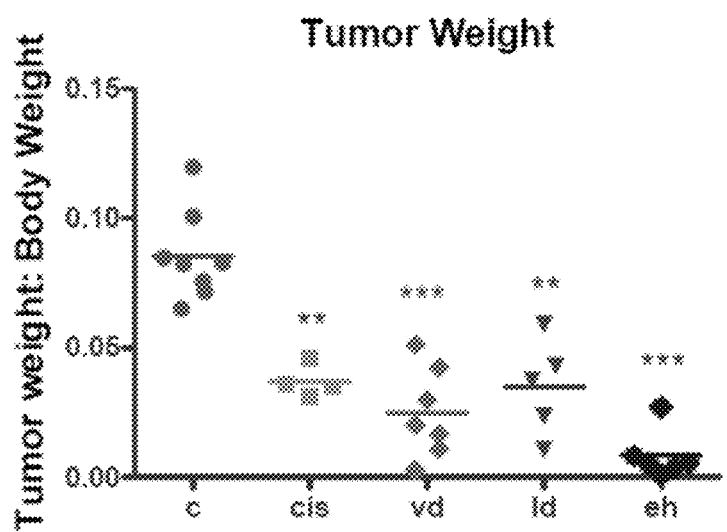
FIG. 1 is a graph of the ratio of tumor weight to body weight after different treatments. The graph shows a smaller tumor burden after consumption of probiotics as food supplement in a prevention model. Male 5-6 week old C57BL6/N mice were fed with probiotics daily starting 1 week before subcutaneous injection of mouse hepatoma cell line Hepa1-6. The animals were sacrificed 38 days after tumor injection to determine tumor:body weight ratio. Tumor burden of probiotics groups were significantly smaller than the control as determined by Tukey's multiple comparison test, but were indifferent between heat-inactivated and viable bacteria. *$p<0.05$. $p<0.01$. *$p<0.001$. C: negative control; cis: cisplatin (0.25 mg/ml every 3 days); vd: heat-inactivated VSL#3® (1010 cfu/d); ld: heat-inactivated LGG (108 cfu/d); eh: viable high dose EcN (108 cfu/d).
Figure 2A:
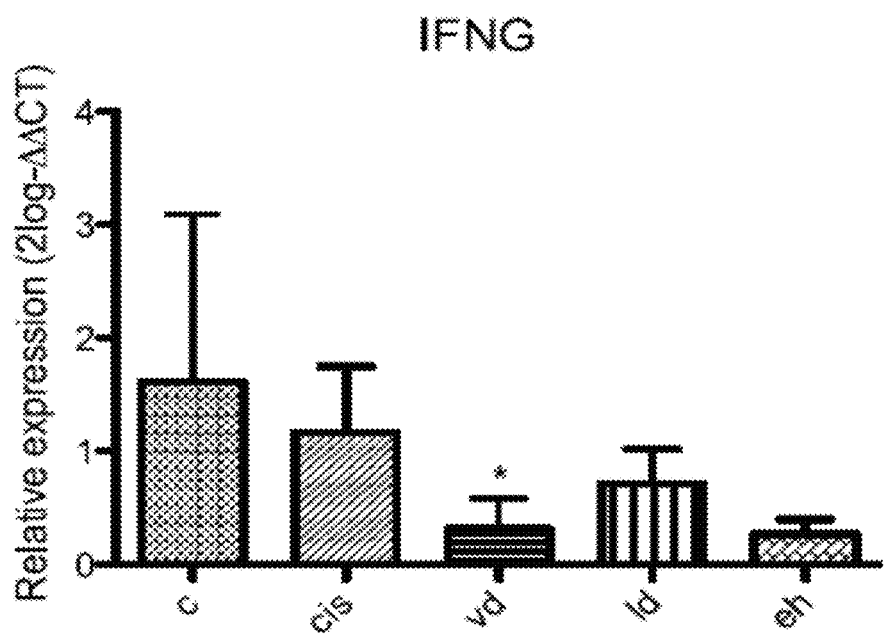
FIGS. 2A-2F show graphs of the relative mRNA expression of T helper cell subset markers, IFNG (FIG. 2A), TBET (FIG. 2B), TGFB-1 (FIG. 2C), FoxP3 (FIG. 2D), IL-17A (FIG. 2E), and RORγt (FIG. 2F), in tumor tissues after consumption of probiotics as food supplement in a prevention model.
Figure 2B:
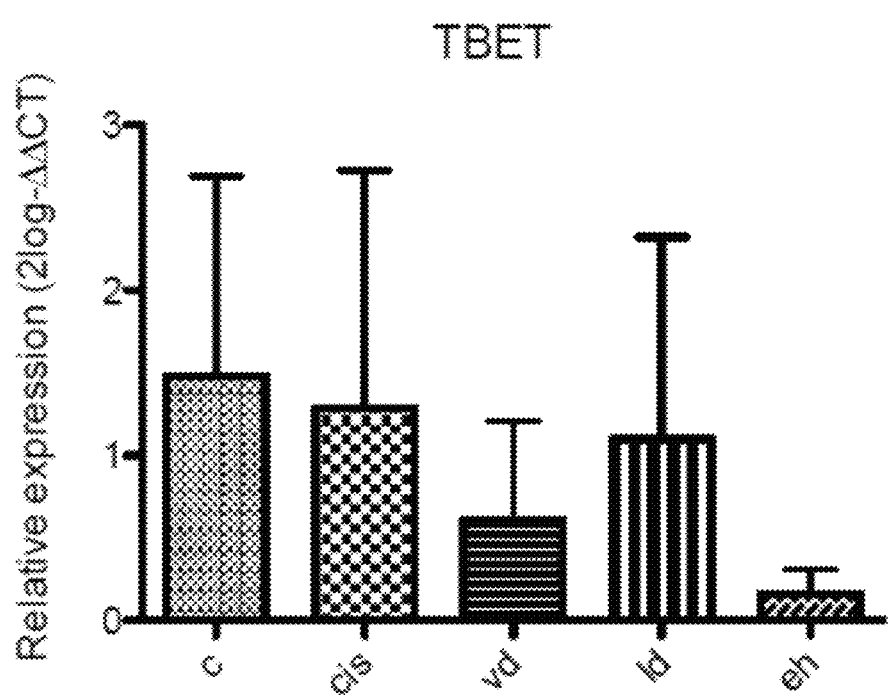
Figure 2C:
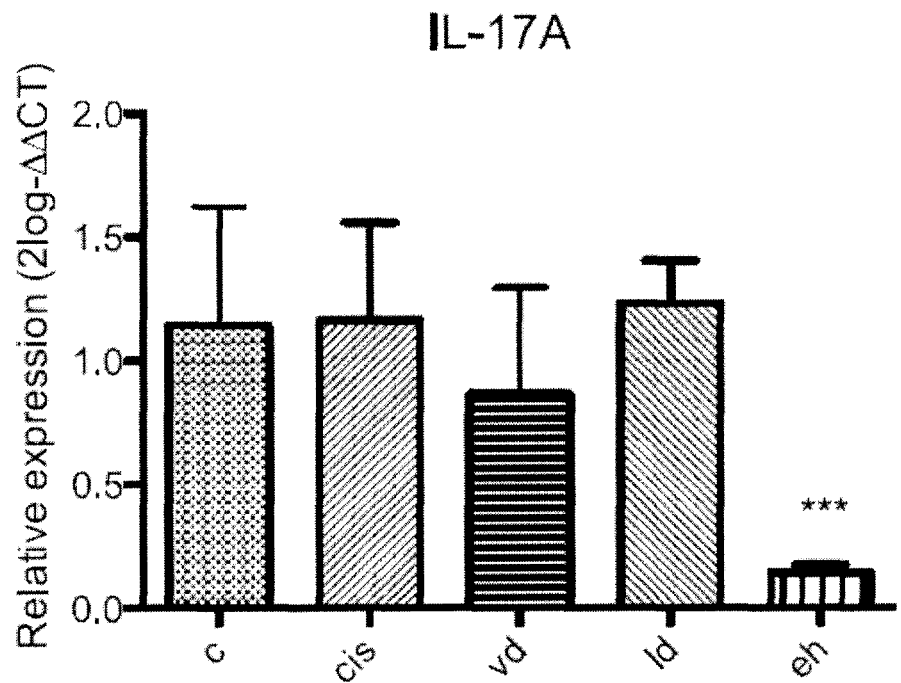
Figure 2D:
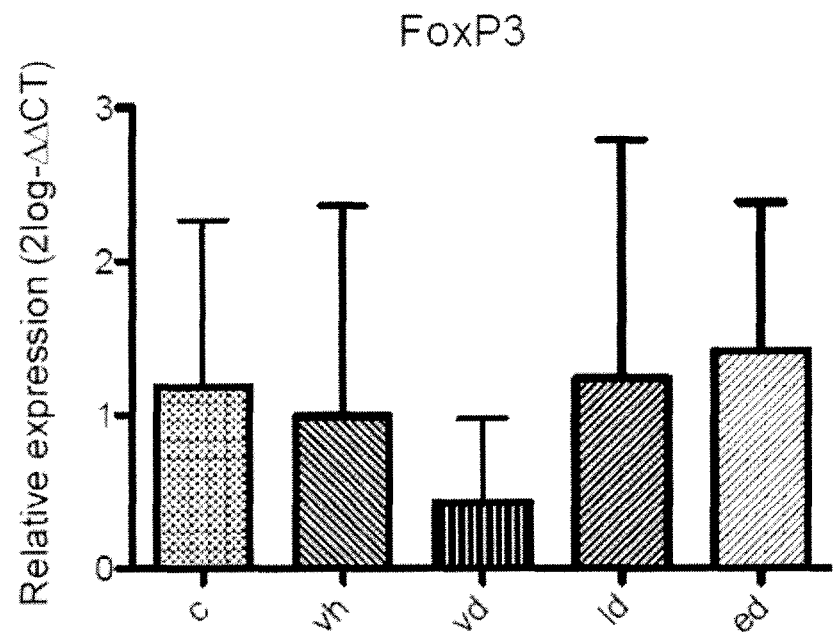
Figure 2E:
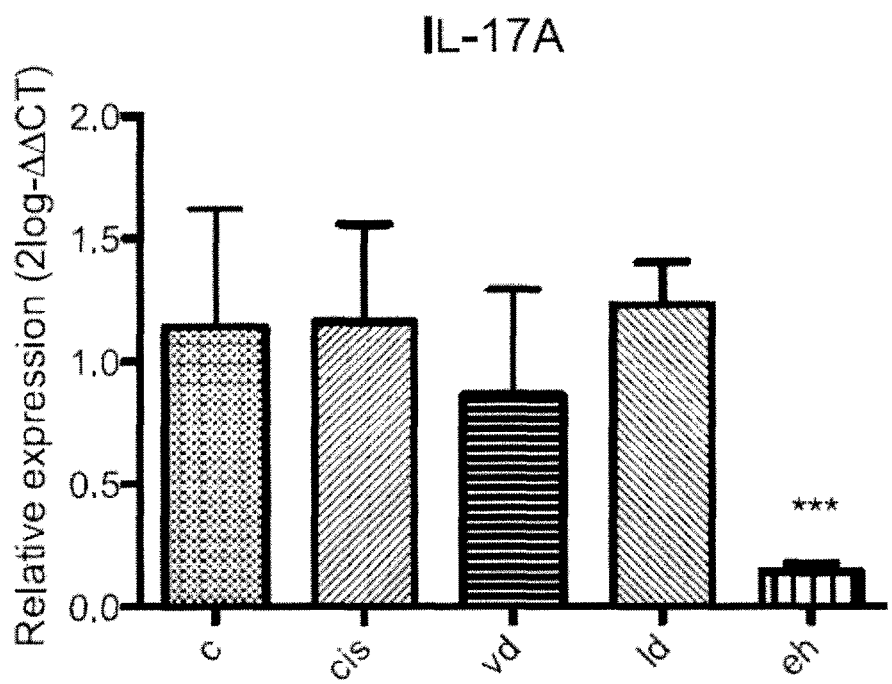
Figure 2F:
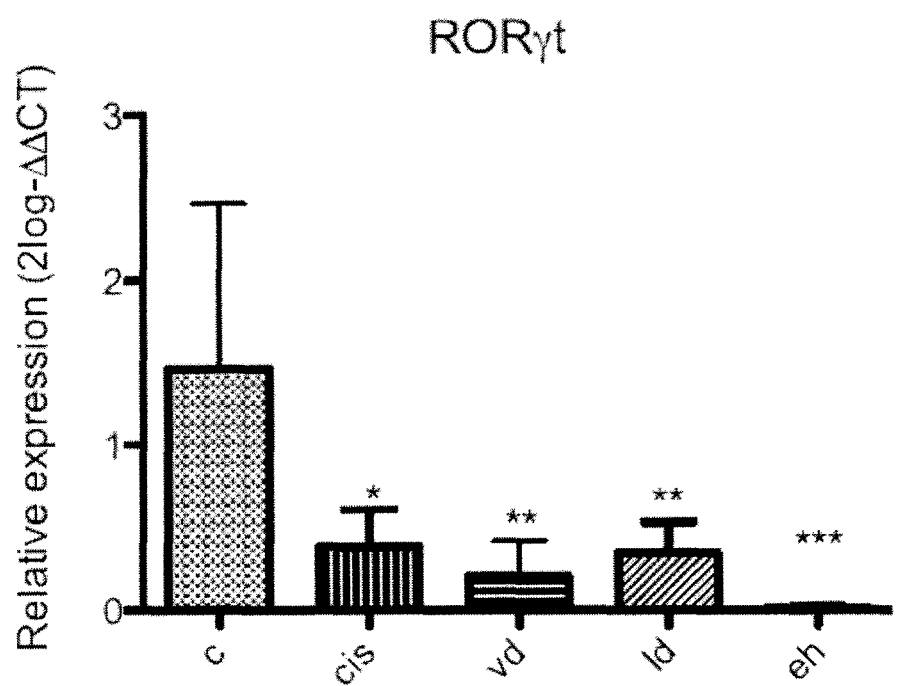
Figure 2G:
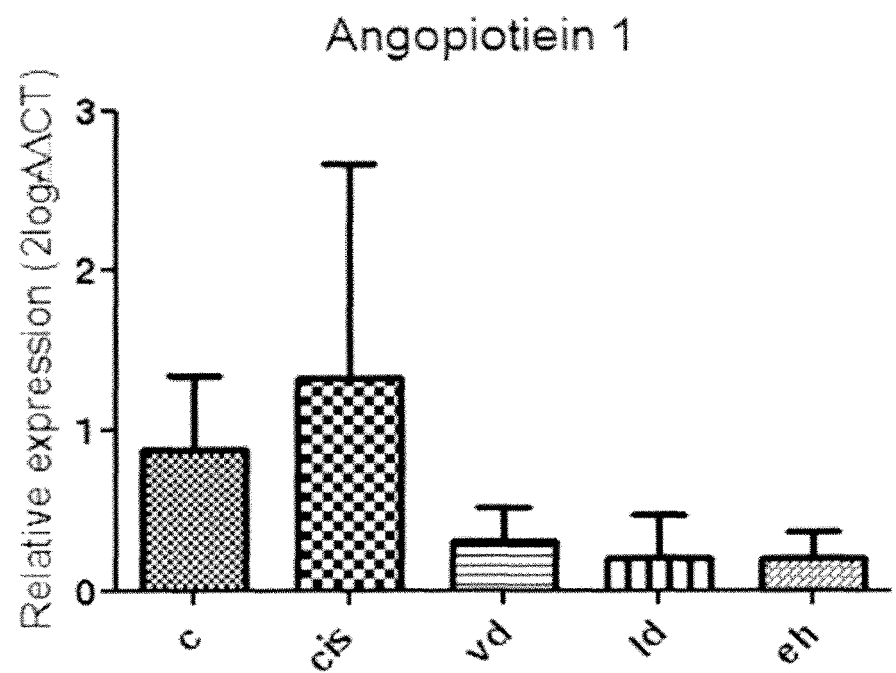
FIGS. 2G-2L show graphs of the relative mRNA expression of angiogenic markers, Angopiotiein 1 (FIG. 2G), Angopiotiein 2 (FIG. 2H), KDR (FIG. 2I), FLT (FIG. 2J), Pecam-1 (FIG. 2K), and VE-cadherin (FIG. 2L), in tumor tissues after consumption of probiotics as food supplement in a prevention model. Expression levels in probiotic groups were compared to control by Dunnett's test. Reduced expression of angiogenic markers could generally be observed along with decreased Treg marker (TGFB-1) and Th17 marker (RORγt) expression, but not with Th1 marker (IFNG, TBET) expression. *$p<0.05$, $p<0.01$, **$p<0.0001$. c: control; cis: cisplatin; vd: heat-inactivated VSL#3®; ld: heat-inactivated LGG (108 cfu/d); eh: viable high dose EcN (108 cfu/d).
Figure 2H:
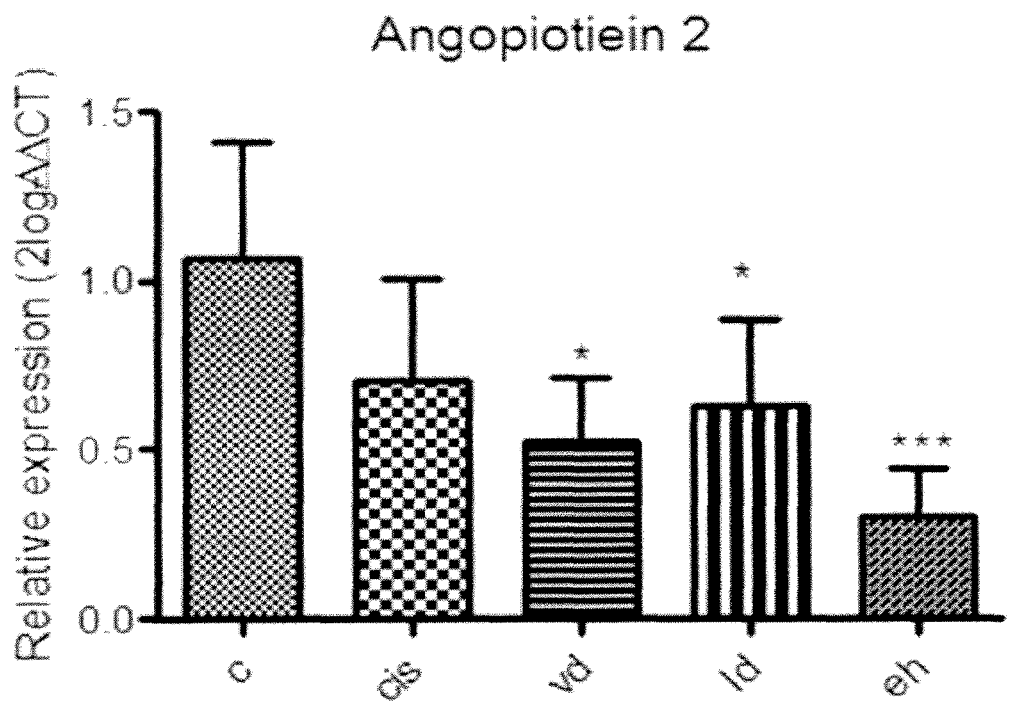
Figure 2I:
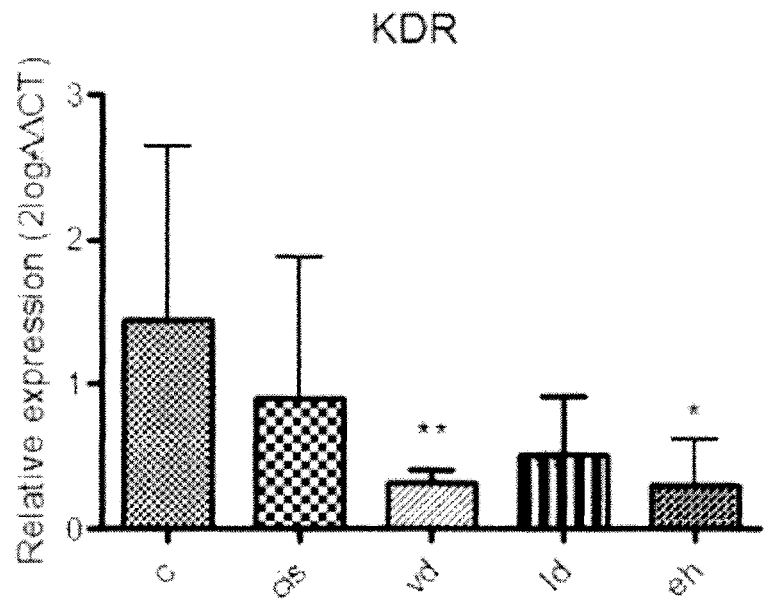
Figure 2J:
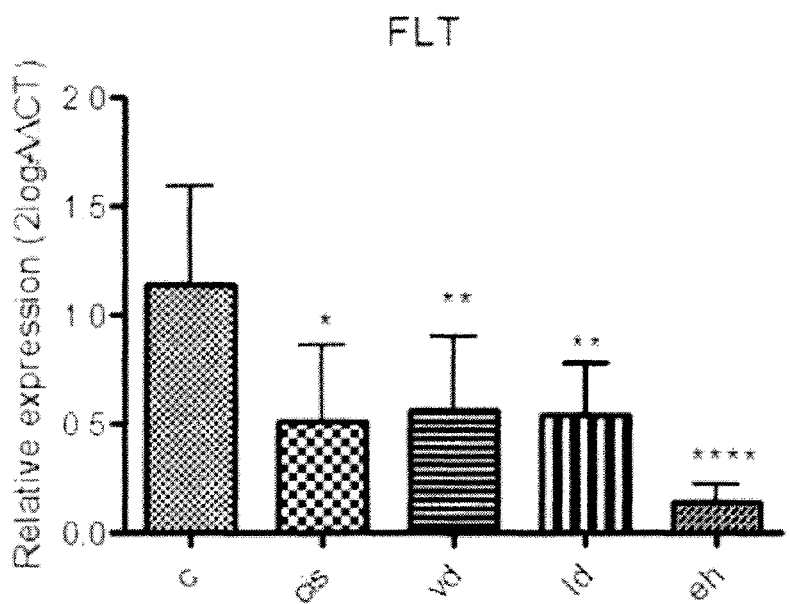
Figure 2K:
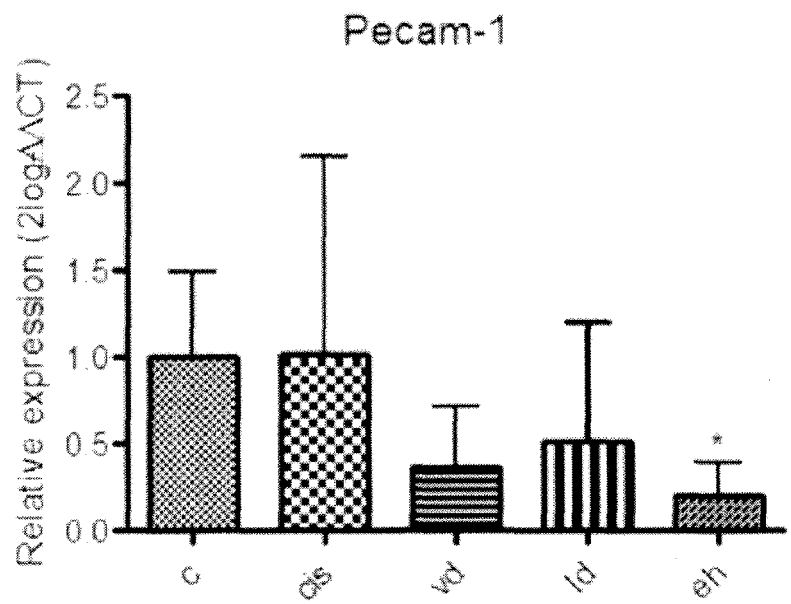
Figure 2L:
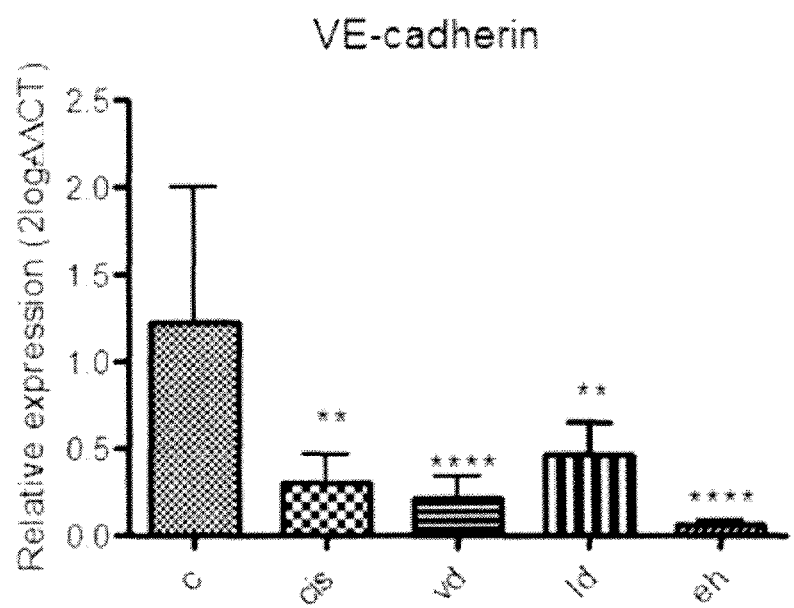

The disclosed method and compositions may be understood more readily by reference to the following detailed description of particular embodiments and the Examples included therein and to the Figures and their previous and following description.

Disclosed are materials, compositions and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a probiotic composition is disclosed and discussed and a number of modifications that can be made to a number of components including the probiotic bacteria are discussed, each and every combination and permutation of probiotic bacteria and the modifications that are possible are specifically contemplated unless specifically indicated to the contrary. Thus, if a class of bacteria A, B, and C are disclosed as well as a class of food D, E, and F and an example of a combination components, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A probiotic formulation, termed ProHep, useful as a food supplement and therapeutic agent for reducing HCC tumor growth, is contemplated. The probiotic formulation comprises a mixture of beneficial probiotic microflora comprising (a) heat-inactivated *Lactobacillus rhamnosus* GG deposited under accession number ATCC 53103, also known as, *Lactobacillus acidophilus* (Moro) Hansen and Macquot, (b) viable *Escherichia coli* Nissle 1917, and (c) heat-inactivated VSL#3®. VSL#3® is a commercially available product traded under the name VSL#3® and comprised of 8 different bacterial strains: *Bifidobacterium breve, Bifidobacterium longum, Bifidobacillus infantis, Lactobacillus acidophilus, Lactobacillus plantarum, Lactobacillus paracasei, Lactobacillus bulgaricus* and *Streptococcus thermophiles*. It was determined that this probiotic formulation can reduce HCC tumor growth.

The major shortcoming of current HCC treatment is the high healthcare cost. For example, molecular targeted therapy using sorafenib, as recommended by the NCCN/AASLD/JSH/ESMO Guideline, is expensive, with an average cost around US$6,000 per month (Cabrera, R. and D. Nelson, *Review article: the management of hepatocellular carcinoma*. Alimentary pharmacology & therapeutics, 2010. 31(4): p. 461-476), so it can only be performed in countries with extensive financial resources for healthcare services (Benson 3rd, A., et al., *NCCN clinical practice guidelines in oncology: hepatobiliary cancers*. Journal of the National Comprehensive Cancer Network: JNCCN, 2009. 7(4): p. 350; Jelic, S., *Hepatocellular carcinoma: ESMO clinical recommendations for diagnosis, treatment and follow-up*. Annals of Oncology, 2009. 20(suppl 4): p. iv41-iv45; Izumi, N., *Diagnostic and treatment algorithm of the Japanese society of hepatology: a consensus-based practice guideline*. Oncology, 2010. 78(Suppl. 1): p. 78-86; Bruix, J. and M. Sherman, *Management of hepatocellular carcinoma: an update*. Hepatology, 2011. 53(3): p. 1020-1022). Published cost analysis of HCC in the United States indicates that the mean 5-year net cost is US$45,000 for an average HCC patient per month (Yabroff, K. R., et al., *Cost of care for elderly cancer patients in the United States*. Journal of the National Cancer Institute, 2008. 100(9): p. 630-641). Meanwhile, probiotics are commonly found in dairy food products, and the cost is only approximately US$86.00 per month for buying patented commercial products such as VSL#3®. Thus, the disclosed effective probiotics offer a cheaper approach in HCC intervention.

Probiotic oral supplementation, whether in viable or heat-inactivated form, was not previously used to treat HCC and was not previously known to reduce HCC growth. Further, although probiotics had shown some general immunomodulatory effects, T helper cell related immunomodulatory effects in HCC tumor microenvironment and its relationship to HCC prevention and intervention were not studied prior to the present work. Specifically, it was not previously known that LGG, EcN and VSL#3® could have an effect on HCC.

The disclosed compositions and methods can also be used to treat those at risk of developing HCC. Etiological factors of HCC include chronic infections with the hepatitis B virus (HBV) or hepatitis C virus (HCV), exposure to dietary aflatoxin B1 (AFB1), and alcohol consumption. Among which, HBV is responsible for 50%-80% of HCC cases worldwide, whereas 10%-25% of cases are thought to be a result of HCV infection (Venook, A. P., et al., *The incidence and epidemiology of hepatocellular carcinoma: a global and regional perspective*. The Oncologist, 2010. 15(Supplement 4): p. 5-13; Block, T. M., et al., *Molecular viral oncology of hepatocellular carcinoma*. Oncogene, 2003. 22(33): p. 5093-5107; Anthony, P., *Hepatocellular carcinoma: an overview*. Histopathology, 2001. 39(2): p. 109-118). The disclosed probiotic compositions can reduce the risk of developing HCC by modulating the immune system by oral consumption of the probiotics before HCC is developed. Thus, hepatitis carriers can be treated with the disclosed probiotic compositions to help reduce their risk of developing HCC. The World Health Organization (WHO) estimates that more than 520 million people in the world are chronic hepatitis virus carriers who are at risk of developing liver cirrhosis and/or liver cancer (WHO. *Hepatitis B Global Alert and Response*. 2013 [cited 2013; Available on webpage who.int/csr/disease/hepatitis/whocdscsrlyo20022/en/index3.html; WHO. *Hepatitis C. Global Alert and Response*. 2013; Available on webpage who.int/csr/disease/hepatitis/whocdscsrlyo2003/en/index4.html). Given the average cost for monthly probiotic consumption is around US$68.30 (Ferring. *VSL#3® ordering*. 2013; Available on webpage vsl3.co.uk/order_vsl3; Mutaflor. *Buy Mutaflor*. 2013; Available on webpage mutaflor.ca/products-page/; verkkoapteekki, *Gefilus*. 2013), the estimated market size for a treatment of 45 days with the disclosed probiotics is about US$44 billion per year.

The disclosed compositions and methods allow the source of chronic microbial challenge to the host to be targeted, which will help to modulate T helper cell related immune response in tumor microenvironment and reduce liver cancer progression. Disclosed are methods for reducing HCC tumor growth using probiotics and methods to reduce tumor growth using a new mixture of probiotics (ProHep). By preventing or treating problems associated with tumor growth in a patient, subsequent health problems can be prevented or mitigated, which can result in reduced health care costs for the patient in the future.

Some of the disclosed probiotic compositions are mixtures of bacteria. For example, some probiotic compositions can be mixtures of several commercially available or public domain bacteria, namely, *Lactobacillus rhamnosus* GG deposited under accession number ATCC 53103, also known as, *Lactobacillus acidophilus* (Moro) Hansen and Macquot, *Escherichia coli* Nissle 1917 (commercially available product traded under the name Mutaflor), VSL#3® (commercially available product traded under the name VSL#3®). The bacterial mixture is a mix of viable and heat-inactivated bacteria, the mixture can be referred to as ProHep. The probiotic components can also be formulated in two or more separate compositions. Such separate compositions can be administered together or separately, at the same time or at different times. The disclosed compositions can further comprise, or can be administered with, other components of compositions. For example, the disclosed probiotic compositions can be combined with food or can be administered with food.

While not wishing to be limited to a particular manner of operation, the disclosed compositions and methods may reduce HCC tumor growth by influencing T helper cells—related immune responses in the tumor microenvironment and angiogenesis (Sung C Y, L. N., El-Nezami H., *Regulation of T helper 17 by bacteria: an approach for the treatment of hepatocellular carcinoma*. International journal of Hepatology, 2012. 2012(Article ID 439024): p. 8).

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Probiotic Compositions

Disclosed are probiotic compositions useful for treating hepatocellular carcinoma (HCC). The disclosed probiotic compositions are probiotic formulations useful as a food supplement and therapeutic agent for reducing HCC risk and/or growth and generally comprise a mixture of beneficial probiotic microflora. It was observed that certain combinations of probiotic bacteria can reduce the risk and/or effect of HCC. Some of the probiotic compositions comprise heat-inactivated *Lactobacillus rhamnosus* GG deposited under accession number ATCC 53103, also known as, *Lactobacillus acidophilus* (Moro) Hansen and Macquot, viable *Escherichia coli* Nissle 1917, and heat-inactivated VSL#3®. For example, the probiotic composition can comprise *Lactobacillus rhamnosus* GG deposited under accession number ATCC 53103, also known as, *Lactobacillus acidophilus* (Moro) Hansen and Macquot (heat-inactivated, 2×1010 cfu/d); *Bifidobacterium breve, Bifidobacterium longum, Bifidobacterium infantis, Lactobacillus acidophilus, Lactobacillus plantarum, Lactobacillus paracasei, Lactobacillus bulgaricus* and *Streptococcus thermophiles*, commercially known as VSL#3® (heat-inactivated, total dose 1.8×1012 cfu/d); and *Escherichia coli* Nissle 1917 (viable, 5×1012 cfu/d). The combination of bacteria can be effective to reduce hepatocellular carcinoma (HCC) growth compared to control growth. The combination of bacteria can be effective to reduce hepatocellular carcinoma (HCC) risk compared to control risk. The bacteria (a), (b), and (c) can each be independently present in the probiotic composition at a concentration of about 20-55 weight percent.

*Lactobacillus acidophilus* (Moro) Hansen and Mocqu (ATCC 53103) are bacteria that are known to modulate production of cytokines relating to Th1/Th2 response, induce T-cell hyporesponsiveness and reduce inflammation in systemic and gut diseases models.

*Escherichia coli* Nissle 1917 are known bacteria that can induce T-cell hyporesponsiveness and promote anti-inflammation.

VSL#3® (Sigma-Tau) are a patented, commercially available probiotic mixture composed of eight bacteria: *Bifidobacterium breve, Bifidobacterium longum, Bifidobacterium infantis, Lactobacillus acidophilus, Lactobacillus plantarum, Lactobacillus paracasei, Lactobacillus bulgaricus*, and *Streptococcus thermophiles*. VSL#3® may promote anti-inflammation by increasing production of anti-inflammatory cytokines, expand Treg pool and decrease levels of proinflammatory cytokines.

These three probiotic strains and probiotic mixture may each, individually, be present in the probiotic composition at a concentration from about 20 to about 55 weight percent. Examples of combinations of concentrations of *Lactobacillus rhamnosus* GG deposited under accession number ATCC 53103, also known as, *Lactobacillus acidophilus* (Moro) Hansen and Macquot, *Escherichia coli* Nissle 1917 (EcN), and VSL#3® in the probiotic composition are listed in Table 1.

TABLE 1

Concentrations of Probiotic Bacteria
(in weight percent of composition)

| Example No. | LGG | EcN | VSL#3 ® |
|---|---|---|---|
| 1 | 20 | 20 | 20 |
| 2 | 20 | 20 | 25 |
| 3 | 20 | 20 | 30 |
| 4 | 20 | 20 | 35 |
| 5 | 20 | 20 | 40 |
| 6 | 20 | 20 | 45 |
| 7 | 20 | 20 | 50 |
| 8 | 20 | 20 | 55 |
| 9 | 20 | 25 | 20 |
| 10 | 20 | 30 | 20 |
| 11 | 20 | 35 | 20 |
| 12 | 20 | 40 | 20 |
| 13 | 20 | 45 | 20 |
| 14 | 20 | 50 | 20 |
| 15 | 20 | 55 | 20 |
| 16 | 25 | 20 | 20 |
| 17 | 30 | 20 | 20 |
| 18 | 35 | 20 | 20 |
| 19 | 40 | 20 | 20 |
| 20 | 45 | 20 | 20 |
| 21 | 50 | 20 | 20 |
| 22 | 55 | 20 | 20 |
| 23 | 30 | 20 | 25 |
| 24 | 30 | 20 | 30 |
| 25 | 30 | 20 | 35 |
| 26 | 30 | 20 | 40 |
| 27 | 30 | 20 | 45 |
| 28 | 30 | 20 | 50 |
| 29 | 30 | 25 | 20 |
| 30 | 30 | 30 | 20 |
| 31 | 30 | 35 | 20 |
| 32 | 30 | 40 | 20 |
| 33 | 30 | 45 | 20 |
| 34 | 30 | 50 | 20 |
| 35 | 40 | 20 | 25 |
| 36 | 40 | 20 | 30 |
| 37 | 40 | 20 | 35 |
| 38 | 40 | 20 | 40 |
| 39 | 40 | 25 | 20 |
| 40 | 40 | 30 | 20 |
| 41 | 40 | 35 | 20 |
| 42 | 40 | 40 | 20 |
| 43 | 50 | 20 | 25 |
| 44 | 50 | 20 | 30 |
| 45 | 50 | 25 | 20 |
| 46 | 50 | 30 | 20 |
| 47 | 55 | 20 | 25 |
| 48 | 55 | 25 | 20 |

The ingredients of the probiotic composition can be mixed together by conventional methods and formed into, for example, tablets for oral administration. Alternatively, the ingredients can be mixed together and placed into gelatin capsules. The disclosed probiotic formulations can also contain conventional food supplement fillers and extenders such as, for example, rice flour. Conveniently, the probiotic formulation can be taken orally at a dosage rate ranging from about 5 milligrams per day to about 50 milligrams per day.

The disclosed probiotic compositions can be formulated as edible, cosmetic or pharmaceutical products. The probiotic compositions can comprise, in addition to the probiotic bacteria, one or more other active agents and/or cosmetically acceptable excipients (in the case of a cosmetic composition), pharmaceutically acceptable excipients (in the case of a pharmaceutical composition) or adequate edible ingredients (in the case of an edible composition). Some probiotic compositions can further comprise one or more active agents. For example, the additional active agent or agents can be other probiotic bacteria that are not antagonistic to the bacteria forming the disclosed probiotic compositions. Depending on the formulation, the bacteria be added as purified bacteria, as a bacterial culture, as part of a bacterial culture, as a bacterial culture which has been post-treated, and alone or together with suitable carriers or ingredients. Prebiotics could also be added.

The disclosed probiotic compositions can be also included in a variety of edible products, such as milk products, yogurt, curd, cheese (e.g., quark, cream, processed, soft and hard), fermented milk, milk powder, milk based fermented product, ice-cream, a fermented cereal based product, milk based powder, a beverage, a dressing, and a pet food. The term "edible product" is used herein in its broadest meaning, including any type of product, in any form of presentation, which can be ingested by an animal, but excluding cosmetic, pharmaceutical, and veterinary products. Examples of other edible products are meat products (e.g., liver paste, frankfurter and salami sausages or meat spreads), chocolate spreads, fillings (e.g., truffle, cream) and frostings, chocolate, confectionery (e.g., caramel, candy, fondants or toffee), baked goods (cakes, pastries), sauces and soups, fruit juices and coffee whiteners. The compositions of the invention could be also used as an ingredient in other food products. Particularly useful edible products are functional foods.

Accordingly, also disclosed are edible compositions that contain the disclosed probiotic composition together with other edible ingredients. The term "edible ingredients" refers to ingredients which are fit to be eaten, i.e. to be used as food, by an animal, preferably but not limited to humans, cattle or pet animals.

Often, probiotic compositions such as those disclosed herein are considered as dietary supplements. Dietary supplements, also known as food supplements or nutritional supplements, provide beneficial ingredients that are not usually ingested in the normal diet. Mostly, dietary supplements are considered as food products, but sometimes they are defined as drugs, natural health products, or nutraceutical products. As used herein, dietary supplements also include nutraceuticals. Dietary supplements are usually sold "over the counter", i.e., without prescription. Some forms of the disclosed probiotic compositions are dietary supplements.

If the probiotic composition is a dietary supplement, it can be administered as such, can be mixed with a suitable drinkable liquid, such as water, yoghurt, milk or fruit juice, or can be mixed with solid or liquid food. In this context the dietary supplement can be in the form of tablets, pills, capsules, lozenges, granules, powders, suspensions, sachets, pastilles, sweets, bars, syrups and corresponding administration forms, usually in the form of a unit dose. For example, the dietary supplement comprising the probiotic composition can be administered in the form of tablets, lozenges, capsules or powders, manufactured in conventional processes of preparing dietary supplements.

The bacteria forming the disclosed probiotic compositions can be in the form of viable cells or non-viable cells. In some embodiments, *Lactobacillus rhamnosus* GG deposited under accession number ATCC 53103, also known as, *Lactobacillus acidophilus* (Moro) Hansen and Macquot and VSL#3® are non-viable and *Escherichia coli* Nissle 1917 are viable cells. Non-viable cells can be produced by, for example, thermally killed micro-organisms or micro-organisms killed by exposure to altered pH, sonication, radiation or subjection to pressure. With non-viable cells, product preparation is simpler, cells may be incorporated easily into commercial products and storage requirements are much less limited than viable cells.

The amount or concentration of bacteria used in the probiotic composition generally can be noted as the amount of colony forming units (cfu) for each strain or combination of strains in the composition. Generally, an effective amount of the bacteria will be an amount that is high enough to significantly modify the condition to be treated in a positive way but low enough to avoid serious side effects (at a reasonable benefit/risk ratio), within the scope of sound medical judgment. An effective amount of the probiotic bacteria can be determined by the skilled artisan and will vary with the particular goal to be achieved, the age and physical condition of the patient being treated, the severity of the underlying disorder, and the final formulation. For example, the bacteria can be present in an amount from about $10^5$ cfu/g to about $10^{12}$ cfu/g, preferably in an amount from about $10^7$ cfu/g to about $10^{11}$ cfu/g. The term "colony forming unit" ("cfu") refers to the number of bacterial cells as revealed by microbiological counts on agar plates. In some probiotic compositions, the probiotic composition comprises between $10^7$-$10^{10}$ cfu/g.

The bacteria for use in the disclosed probiotic compositions can be produced by, for example, cultivating the bacteria in a suitable medium and under suitable conditions. The bacteria can be cultivated alone to form a pure culture, or as a mixed culture together with other microorganisms, or by cultivating bacteria of different types separately and then combining them in the desired proportions. After cultivation, the cell suspension can be recovered and used as such or treated in the desired manner, for instance, by concentrating or freeze-drying, to be further employed in the preparation of the products. Sometimes the probiotic preparation can be subjected to an immobilization or encapsulation process in order to improve the shelf life. Several techniques for immobilization or encapsulation of bacteria are known in the art.

*Lactobacillus rhamnosus* GG deposited under accession number ATCC 53103, also known as, *Lactobacillus acidophilus* (Moro) Hansen and Macquot, *Escherichia coli* Nissle 1917, and VSL#3® can be effective not only when combined in a single composition, but also when used on their own, or in two or more different compositions administered simultaneously, sequentially, or separately after a certain period of time.

"Probiotics" are live microorganisms that when administered in adequate amounts confer a beneficial health effect on the host. Natural intestinal microflora include numerous probiotic microorganisms. Heat-inactivated probiotics refer to probiotics that have been killed by heating. The term "parts by weight," of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, a "weight percent" of a component, unless specifically stated to the contrary, is based on the total weight of the formulation or composition in which the component is included. Thus, for example, a component at a concentration of 20-55 weight percent means that the component constitutes 20-55 percent of the total weight of the composition in which the component is included.

Kits

The materials described above, as well as other materials, can be packaged together in any suitable combination as a kit useful for performing, or aiding in the performance of, the disclosed methods. It is useful if the kit components in a given kit are designed and adapted for use together in the disclosed methods. For example, disclosed are kits for treating a subject at risk of or diagnosed with HCC, the kits comprising heat-inactivated *Lactobacillus rhamnosus* GG deposited under accession number ATCC 53103, also known as, *Lactobacillus acidophilus* (Moro) Hansen and Macquot, viable *Escherichia coli* Nissle 1917, and heat-inactivated VSL#3®.

Methods

Disclosed are methods of treating hepatocellular carcinoma (HCC). The methods comprise orally administering a probiotic composition to a subject at risk of or diagnosed with HCC. The probiotic composition can be administered in any effective schedule. For example, the probiotic composition can be administered daily. The probiotic composition can be administered daily for at least one month. The subject can be diagnosed with HCC. The subject can be at risk of HCC. The subject can be a subject diagnosed with hepatitis B virus, hepatitis C virus, or both. The subject can be a subject exposed to aflatoxin B1 (AFB1). The subject can be a subject diagnosed with alcoholism.

The methods can further comprise, prior to administering the probiotic composition, diagnosing the subject as having HCC. The methods can further comprise, prior to administering the probiotic composition, diagnosing the subject as at risk of HCC. Diagnosing the subject as at risk of HCC can comprise diagnosing the subject as having hepatitis B virus, hepatitis C virus, or both. Diagnosing the subject as at risk of HCC can comprise diagnosing the subject as having been exposed to aflatoxin B1 (AFB1). Diagnosing the subject as at risk of HCC can comprise diagnosing the subject as having alcoholism.

Also disclosed are methods comprising diagnosing the subject as having or being at risk of HCC and orally administering a probiotic composition to the subject diagnosed as having or being at risk of HCC.

Also disclosed are mixtures formed by performing or preparing to perform the disclosed methods. For example, disclosed are mixtures comprising heat-inactivated *Lactobacillus rhamnosus* GG deposited under accession number ATCC 53103, also known as, *Lactobacillus acidophilus* (Moro) Hansen and Macquot, viable *Escherichia coli* Nissle 1917, heat-inactivated VSL#3®. The disclosed probiotic formulations can also be mixtures with, for example, food, food components, and conventional food supplement fillers and extenders such as, for example, rice flour.

Whenever the methods involve mixing or bringing into contact compositions or components or reagents, performing the methods create a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

The terms "one day's treatment", "daily treatment", "daily administration" and "daily intake" are used interchangeably and mean the total dose of the probiotic composition to be taken by or administered to the patient each day in the treatment period. If the treatment is administered by the patient him/herself, the right dose is preferably provided in a suitable container containing the correct dose of the medical product. The total daily dose may advantageously be divided into two or more containers containing the right doses to be taken or administered during the day, for example as the first and the last meal of the day. Alternatively, the patient or the medical staff may measure the right dose for each administration from a larger container comprising the probiotic composition.

The term "reduce the risk" of a condition or event refers to either or both (a) reducing the likelihood or probability of the condition or event occurring or coming into existence compared to a standard or reference likelihood or probability of the condition or event occurring or coming into existence and (b) reducing or ameliorating the amount, size, concentration, severity, rate, stage, progress, and/or other measure of the condition or event if it occurs compared to a standard or reference amount, size, concentration, severity, rate, stage, progress, and/or other measure of the condition or event. For example, reducing the risk of HCC refers to either or both (a) reducing the likelihood or probability of HCC occurring and (b) reducing or ameliorating the amount, size, severity, rate of growth, stage, progress, and/or other measure of HCC severity or stage if HCC occurs. Any one or combination of the effects related to risk can be considered a reduction in the risk of the condition or event. For example, if the rate of growth of HCC once it occurs is lower than a standard or reference rate of growth (such as the rate of growth of an untreated subject with HCC) then the risk of HCC can be said to have been reduced. As another example, if treated subjects without HCC develop HCC at a lower rate than a standard or reference rate then the risk of HCC can be said to have been reduced.

The term "complete oral nutritional supplement" refers to products and formulations that can provide a subject with nutrition orally that is nutritionally complete; that is, that can be used as the sole source of nutrition.

The terms "high," "higher," "increases," "elevates," or "elevation" refer to increases above basal or reference levels, e.g., as compared to a control. The terms "low," "lower," "reduces," or "reduction" refer to decreases below basal or reference levels, e.g., as compared to a control.

The term "reduce" means to lower or decrease in activity, amount, size, weight, rate, stage, severity, expression, or the like. This can be a complete reduction of activity, amount, size, weight, rate, stage, severity, expression, or the like, or a partial reduction of activity, amount, size, weight, rate, stage, severity, expression, or the like. Reduction can be compared to a control or to a standard level. Reduction can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "providing" as used herein refers to any means of adding a compound, molecule, component, or composition to something else, as well as to the act of such addition. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a composition prior to the onset of clinical symptoms of a disease or condition so as to prevent a physical manifestation of aberrations associated with the disease or condition.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

The term "effective amount" of a composition refers to a nontoxic but sufficient amount of the composition to provide the desired result. As discussed elsewhere herein, the exact amount required will vary from subject to subject, depending on the species, age, and general condition of the subject, the mode of administration, and the like. Thus, it is not possible to specify an exact "effective amount." However, an appropriate effective amount can be determined by one of ordinary skill in the art using only routine experimentation.

The dosages or amounts of the disclosed probiotic compositions are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—ProHep Treatment Reduces Tumor Size

The effect of a probiotic mixture of bacteria was tested on an animal model of HCC. Male C57BL/6N mice (5-6 weeks-old) were fed daily with a therapeutically effective amount of probiotics for a total of 45 days, starting one week before subcutaneous tumor inoculation with $1 \times 10^7$ Hepa106 cells. Tumor size was found to be significantly smaller in animals fed with both heat-inactivated bacteria and viable bacteria (FIG. 1). Analysis on VSL#3® groups revealed that smaller tumor size appears to be correlated with lower expression level of Treg marker TGFB (R=0.5, p<0.05), Th17 marker RORC (R=0.5, p<0.05), and angiogenic markers ANGPT2 (R=0.6, p<0.05), TIE1 (R=0.6, p<0.01), VE-cadherin (R=0.7, p<0.005), suggesting that probiotics consumption may modulate T cell subsets in tumor and may this may have an impact on tumor angiogenesis (FIGS. 2A-2L).

Figure 3A:
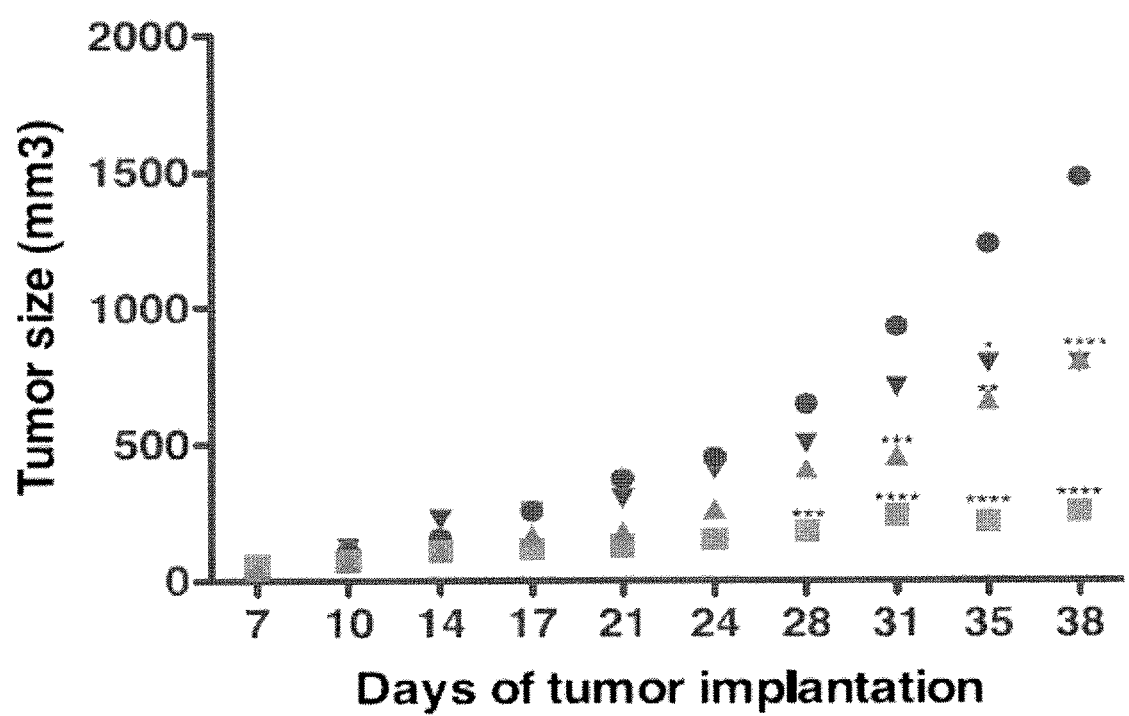
FIG. 3A shows a graph of tumor size and FIG. 3B shows a graph of tumor weight in mice inoculated with $1 \times 10^7$ Hepa1-6 tumor cells subcutaneously and fed with a ProHep diet daily starting from either 1-week before (p: ProHep prevention) or at the same day (pt: ProHep treatment) of tumor inoculation. Cisplatin was given as positive control every 3 days i.p.
Figure 3B:
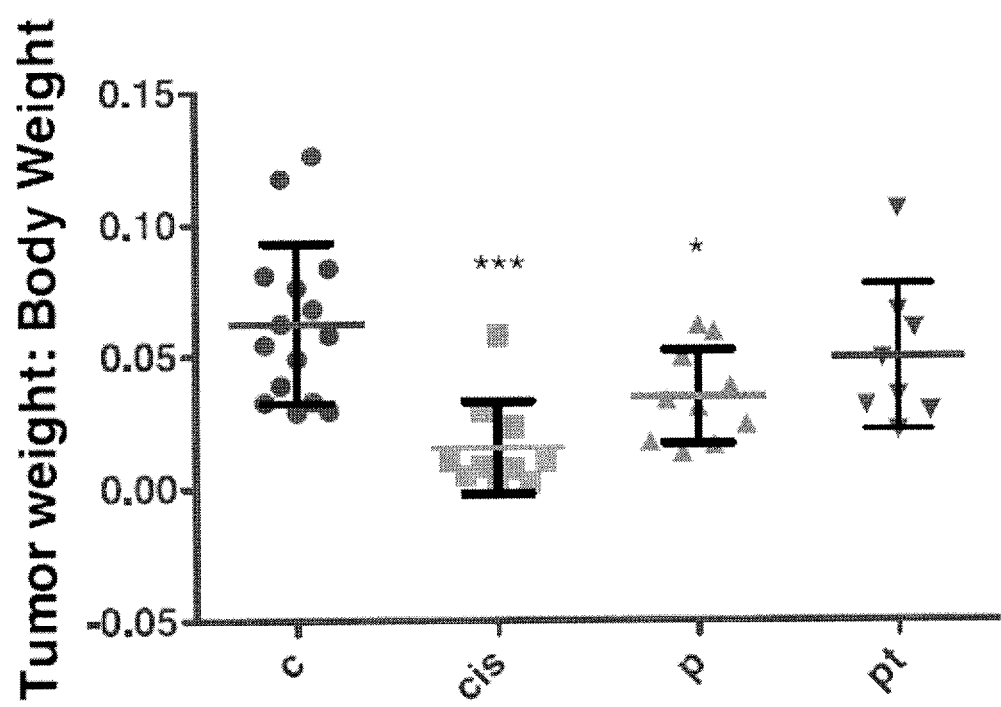

In another study, C57BL6/N mice were inoculated with $1 \times 10^7$ Hepa1-6 tumor cells subcutaneously and tumor sizes were monitored for 38 days with caliper. Mice were fed with a ProHep diet daily starting from either 1-week before (p: ProHep prevention) or at the same day (pt: ProHep treatment) of tumor inoculation. Cisplatin, a common chemotherapeutic drug, was given as positive control at a dose of 0.25 mg/mL every 3 days i.p. Tumor volume was significantly smaller in probiotic groups after 1 month (FIG. 3A). Tumors that were excised at the end of the experiment had a smaller weight in prevention group as compared to control (*p<0.05) (FIG. 3B). Statistical analyses by one-way ANOVA, post-hoc Tukey's multiple comparison test.

Example 2—Tumor Growth is Limited by Increased Hypoxia

Figure 4A:
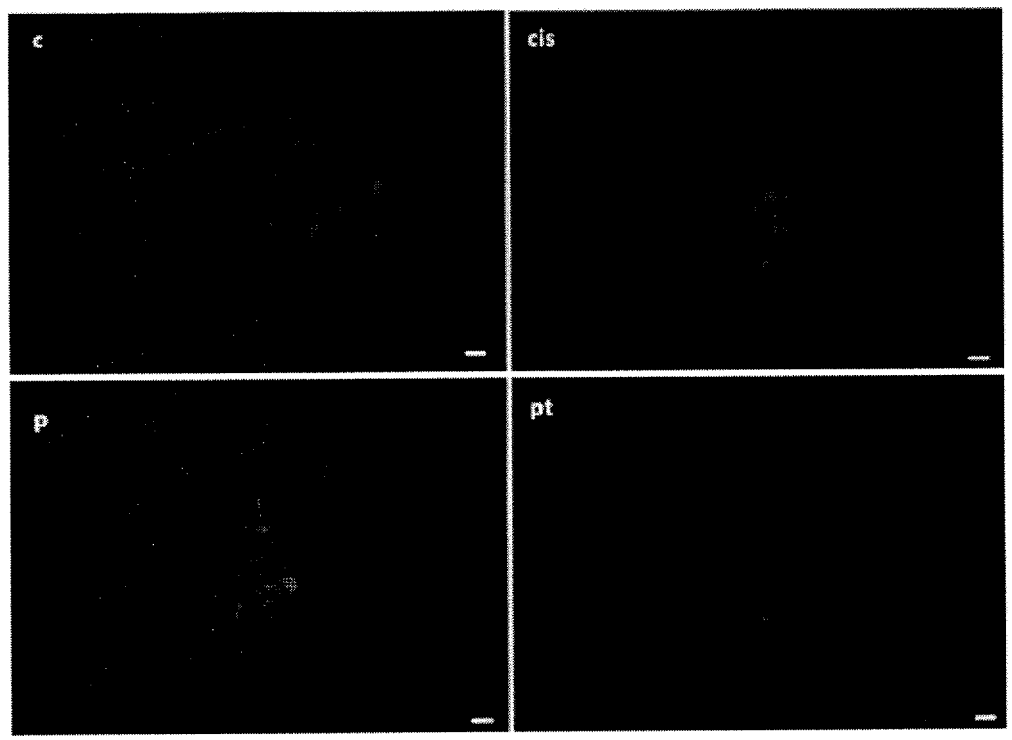
FIG. 4A shows confocal images of whole tumor sections with TO-PRO-3 staining for dead cells. Scale bar, 200 µm.
Figure 4A:
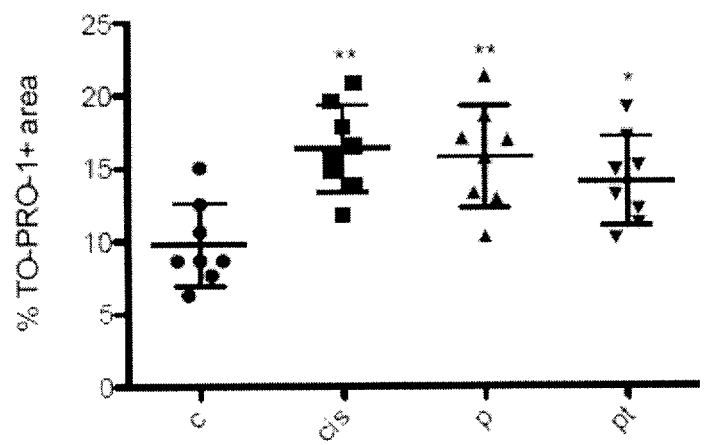
Figure 4B:
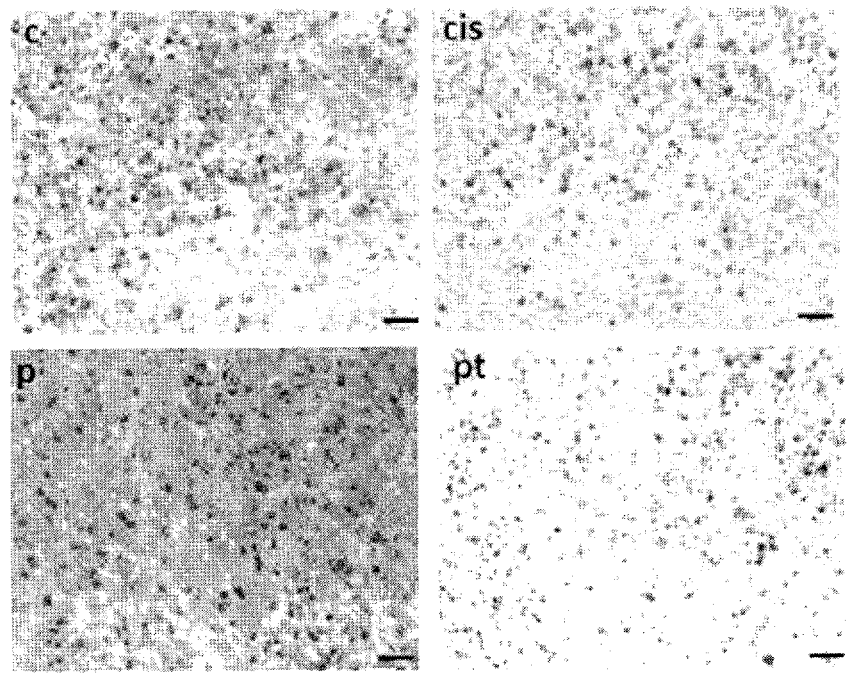
FIGS. 4B-4D show immunostaining for representative tumor sections for Ki67 (FIG. 4B), caspase 3 (FIG. 4C) and GLUT-1 (FIG. 4D) (blue) and CD31 (red) are shown. Scale bar, 50 µm.
Figure 4B:
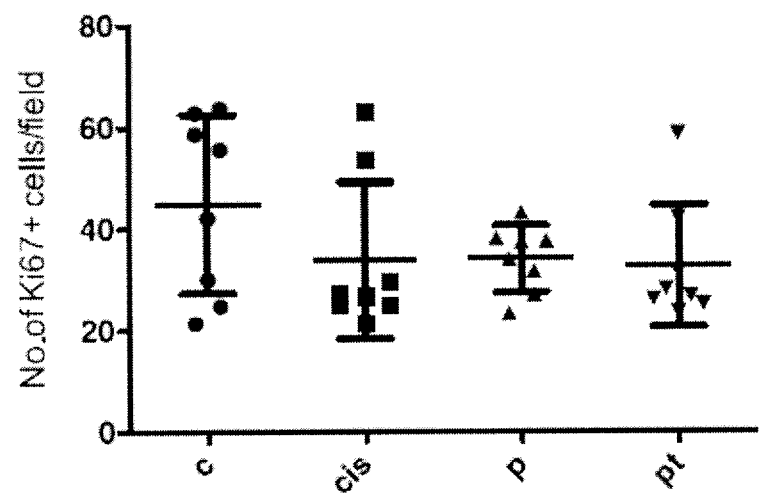
Figure 4C:
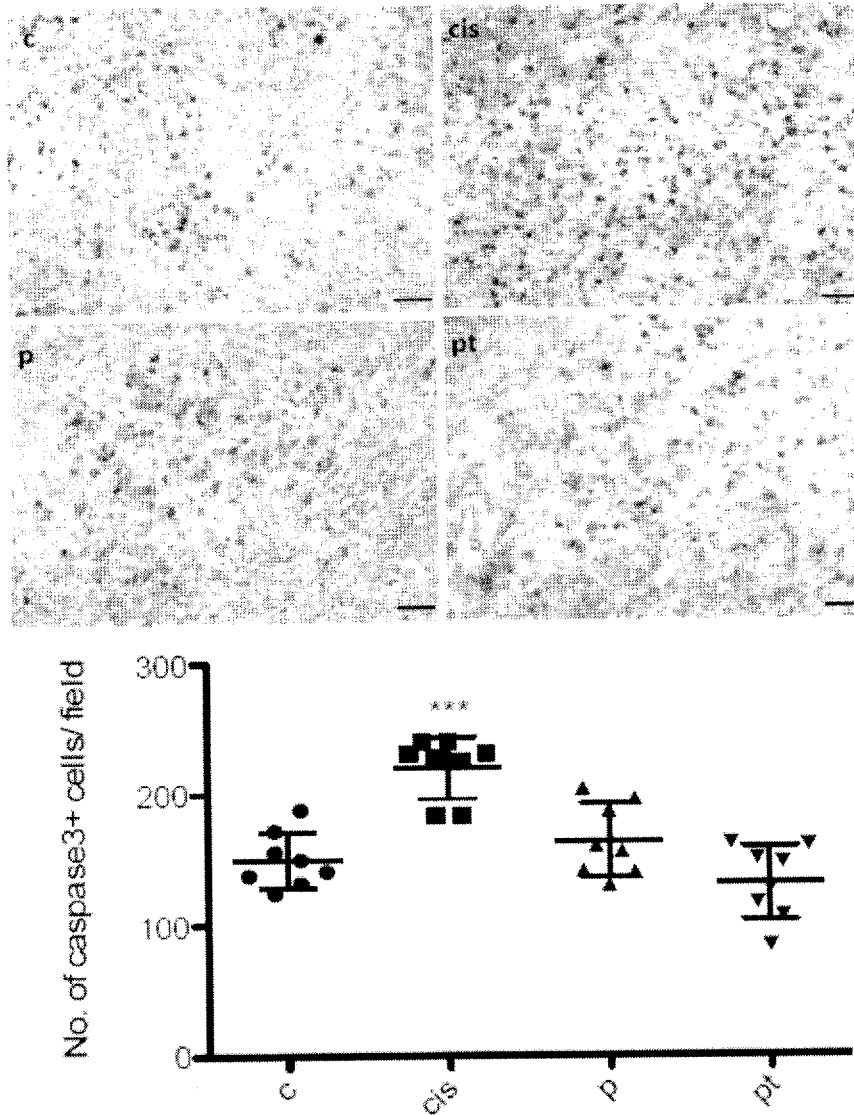
Figure 4D:
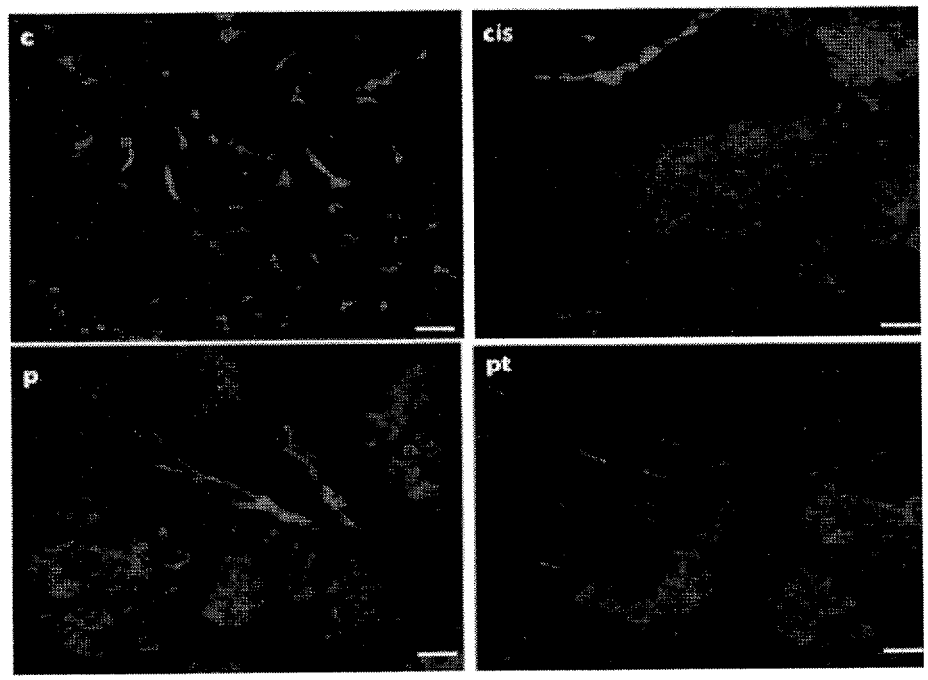
Figure 4D:
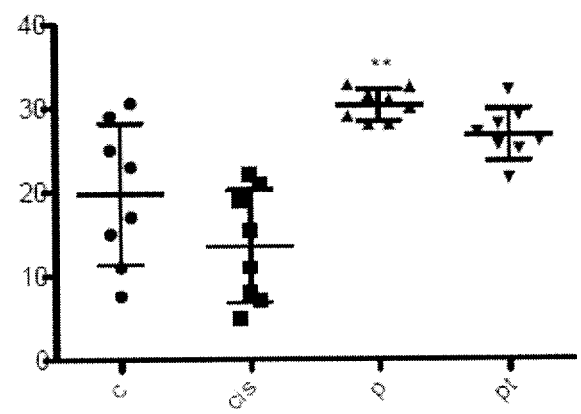

Confocal images of whole tumor sections with TO-PRO-3 staining for dead cells is shown in FIG. 4A. Scale bar, 200

μm. FIGS. 4B-4D show immunostaining for representative tumor sections for Ki67 (FIG. 4B), caspase 3(FIG. 4C) and GLUT-1 (FIG. 4D) (blue) and CD31 (red). Scale bar, 50 μm. Significant increase in area of cell death was observed in ProHep groups, however, there was no significant difference in the number of proliferating cells (Ki67+) and apoptotic cells (caspase-3+), suggesting that reduced tumor size is not related to reduced growth and increased apoptosis, but is related to increased necrosis. Meanwhile, significant increase in hypoxic area (GLUT-1) was found in the ProHep prevention (p) group, suggesting that reduced tumor size is likely to be related to hypoxia-induced cell death.

Example 3—ProHep Inhibits Angiogenesis in a Subcutaneous HCC Model

Figure 5A:
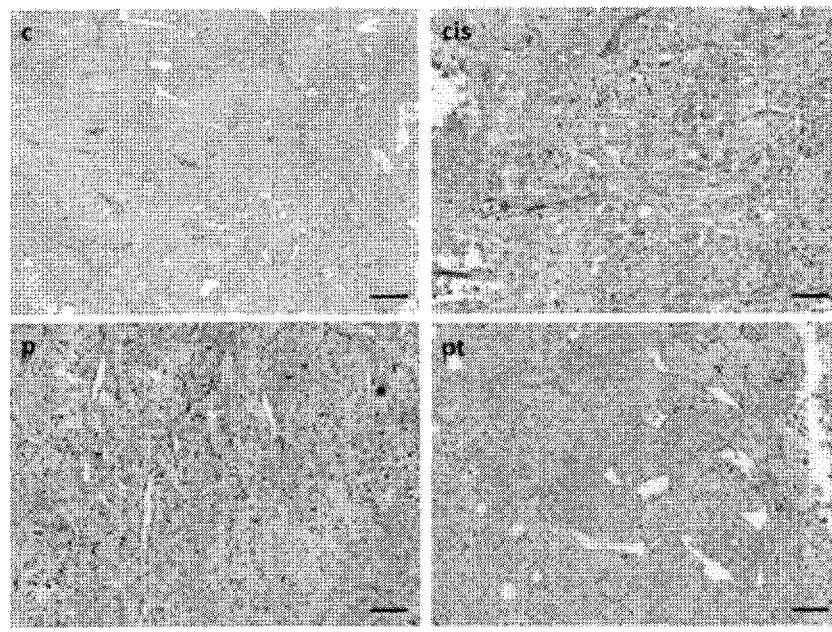
FIG. 5A shows microvessel density of representative tumor sections. Scale bar, 50 µm.
Figure 5A:
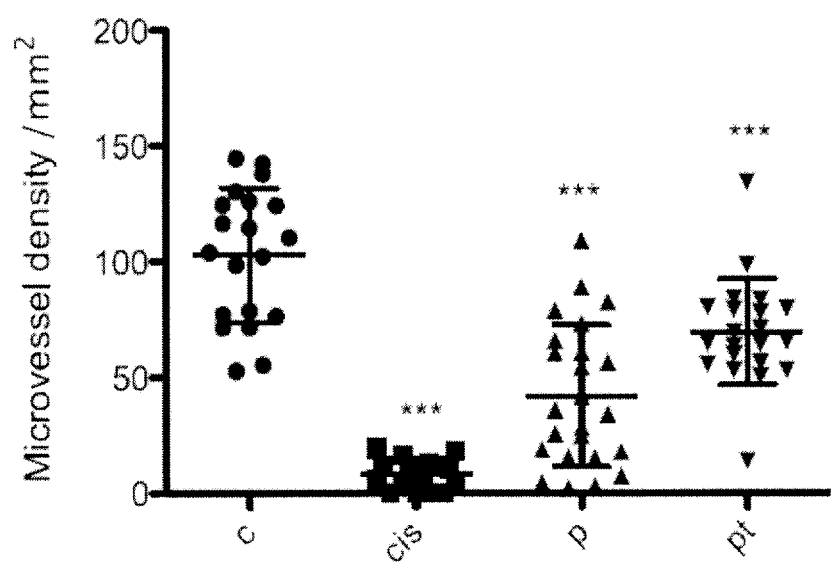
Figure 5B:
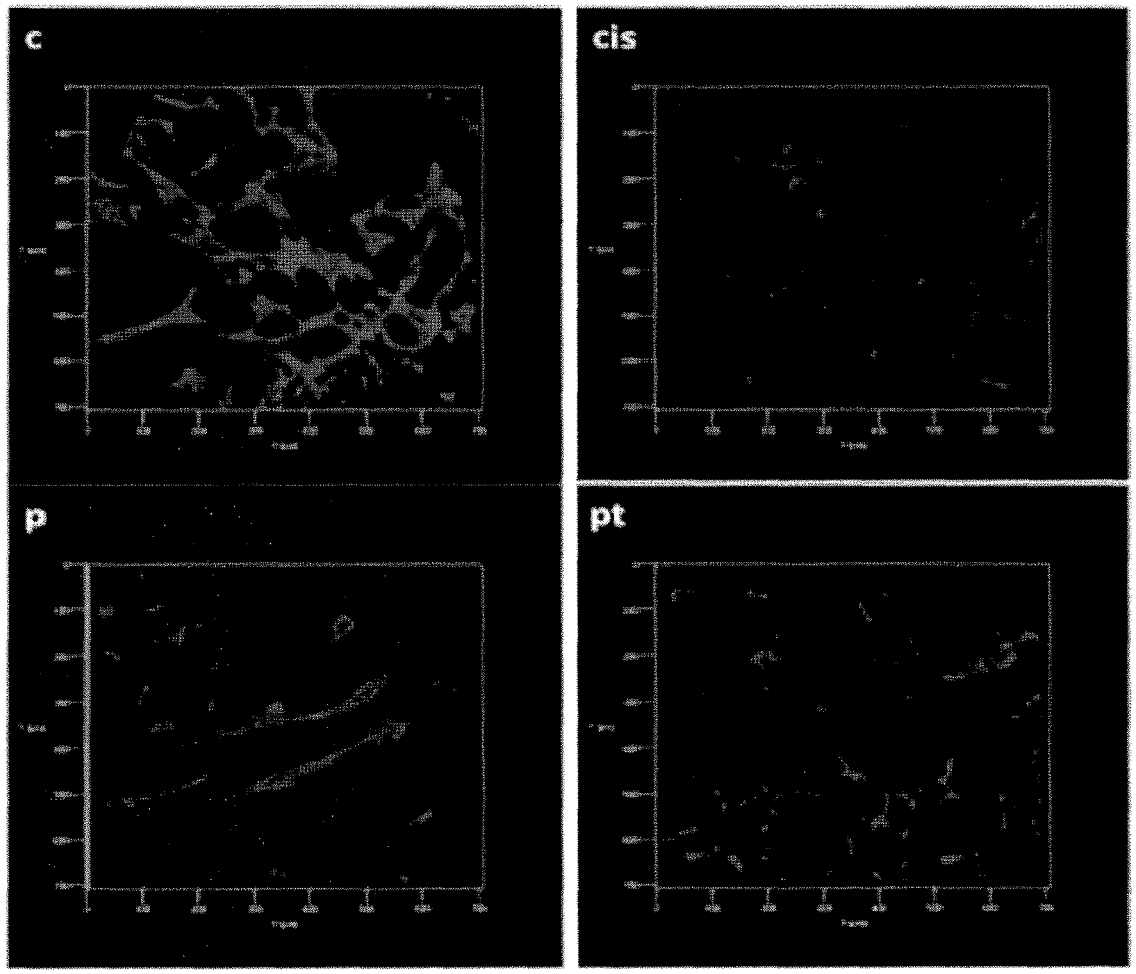
FIG. 5B shows images of three-dimensional models obtained by confocal Z stacks, after superimposition of multiple confocal planes (section thickness, 25 µm).
Figure 5B:
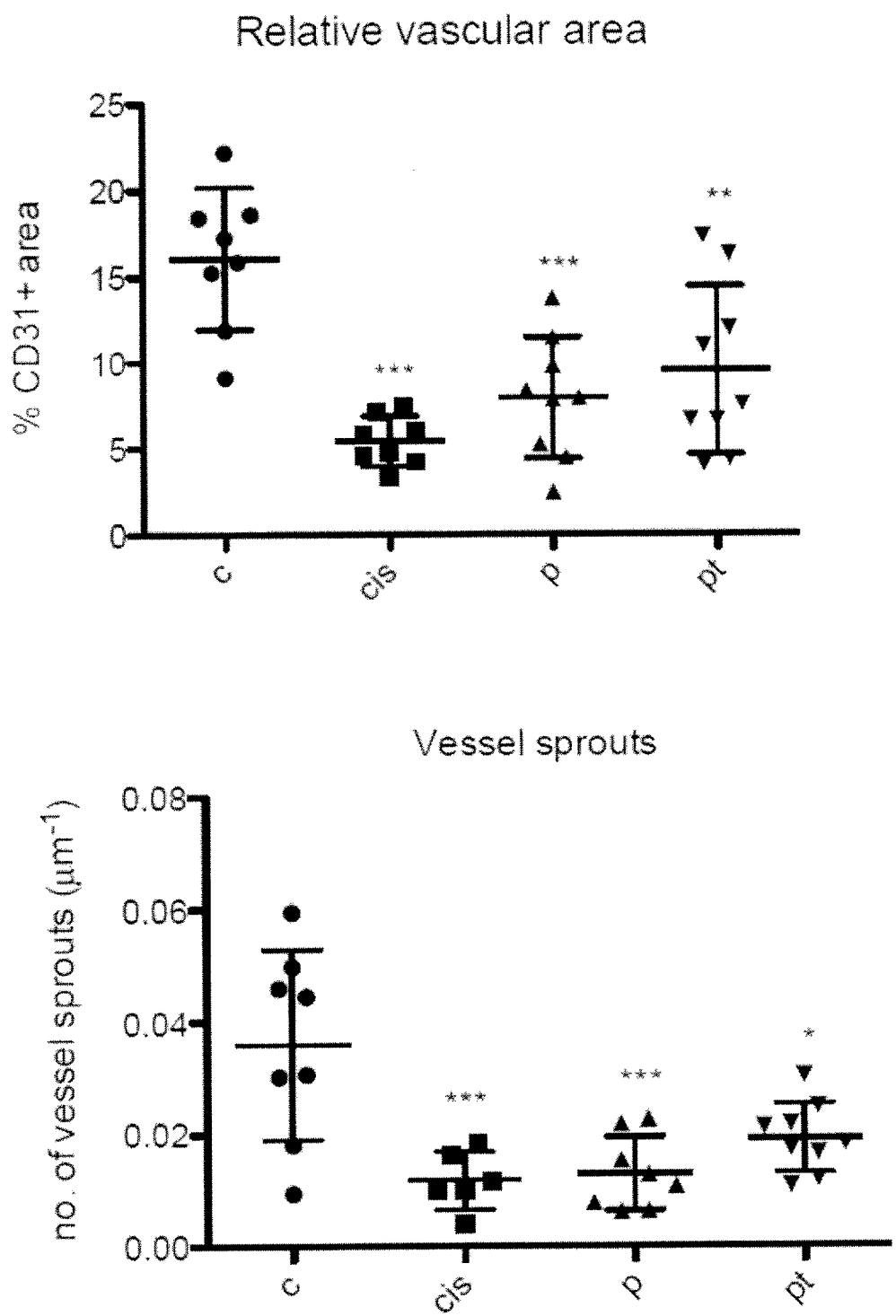

Microvessel density of representative tumor sections is shown in FIG. 5A. FIG. 5B shows images of three-dimensional models obtained by confocal Z stacks, after superimposition of multiple confocal planes. Significantly smaller microvessel density, relative vascular area and vessel sprouting were observed in ProHep groups as compared to control. (*p<0.05; , p<0.01; *, p<0.001).

Figure 6A:
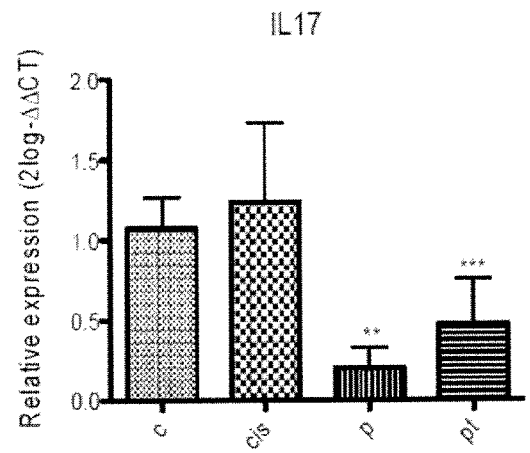
FIGS. 6A-6H show gene expression by real-time quantitative PCR (RT-qPCR) in whole-tumor lysates of IL17 (FIG. 6A), RORγt (FIG. 6B), TGF-β (FIG. 6C), Angopiotiein 2 (FIG. 6D), FLT (FIG. 6E), KDR (FIG. 6F), TEK (FIG. 6G), and VE-cadherin (FIG. 6H). Hprt were used as reference genes.
Figure 6B:
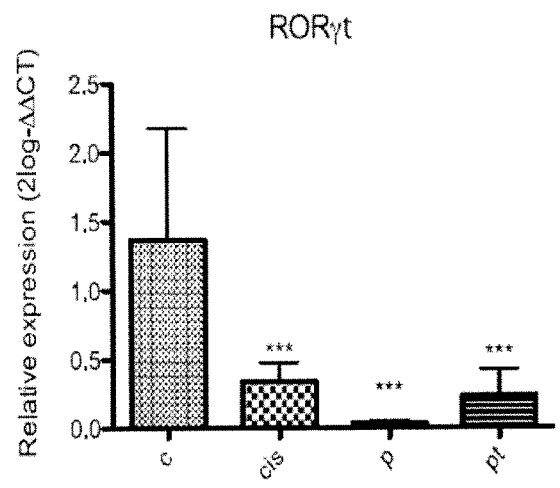
Figure 6C:
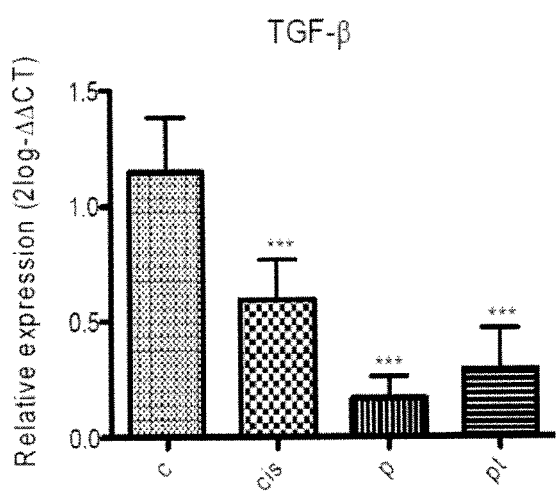
Figure 6D:
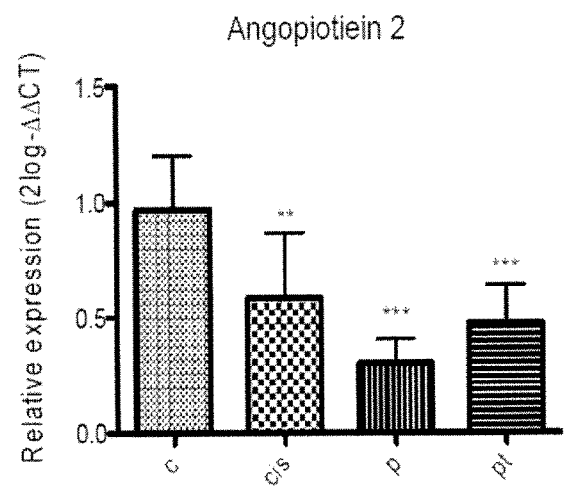
Figure 6E:
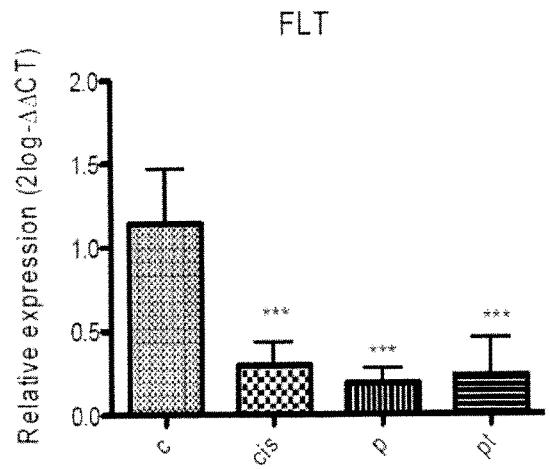
Figure 6F:
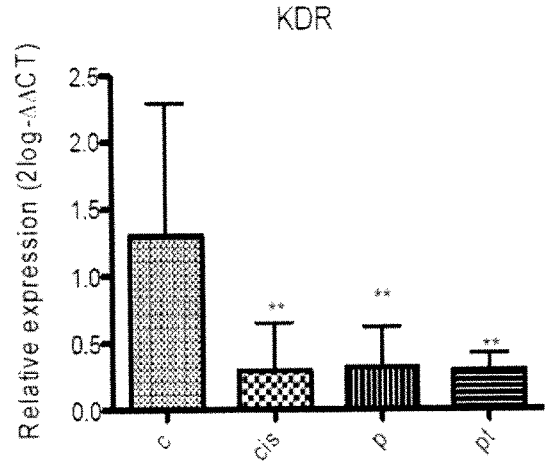
Figure 6G:
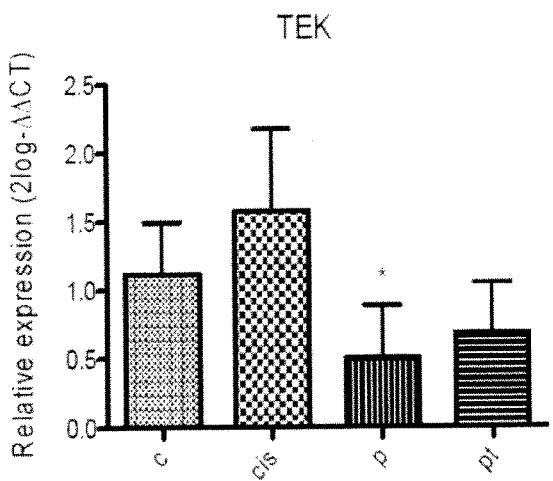
Figure 6H:
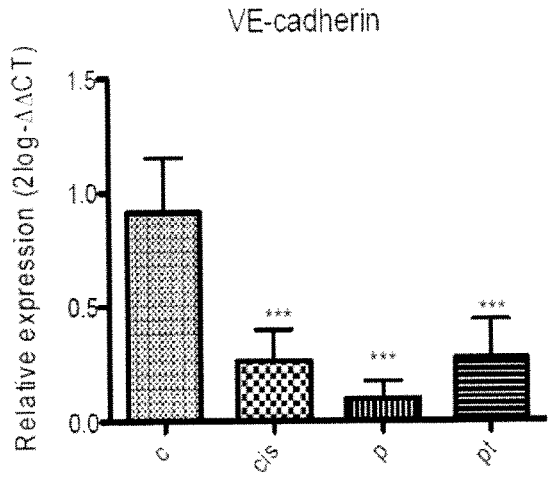
Figure 6I:
FIG. 6I shows the correlation of differential gene expression by hierarchical gene clustering analysis.

Example 4—ProHep Treatment Downregulates the Expression of Proangiogenic Genes in Tumors FIGS. 6A-6H show gene expression by real-time quantitative PCR (RT-qPCR) in whole-tumor lysates. Hprt were used as reference genes. *p<0.05; , p<0.01; *, p<0.001. FIG. 6I shows the correlation of differential gene expression by hierarchical gene clustering analysis. The smaller tumor burden in the ProHep groups may be associated with lower expression level of Th17 (RORC, IL-17) and angiogenic markers (VE-cadherin, ANG2, KDR, FLT, TEK and TGFB).

Example 5—ProHep Prevents Tumor Outgrowth in an IL-17-Dependent Manner

Figure 7A:
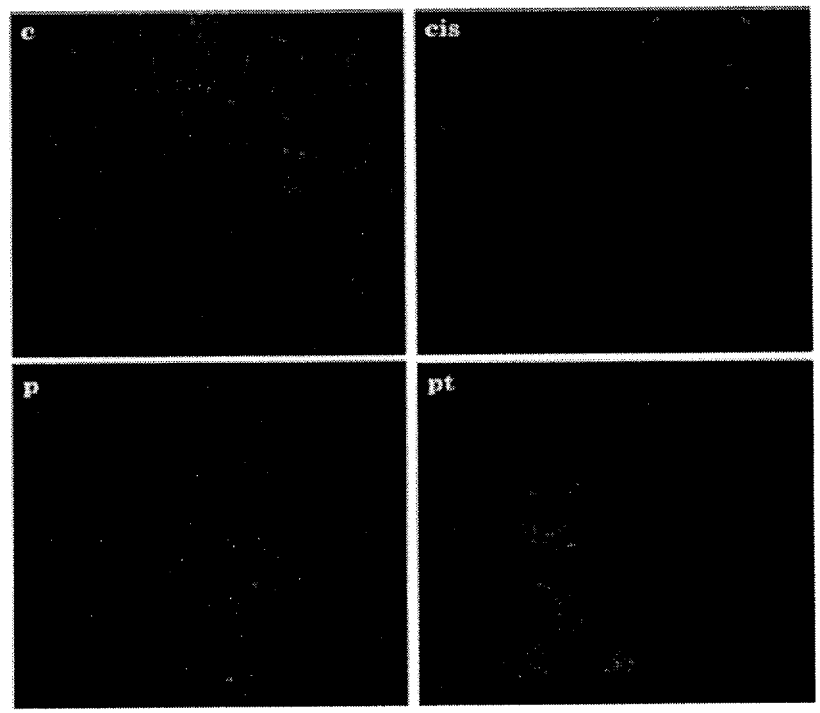
FIG. 7A shows immunostaining of IL-17 in representative tumor sections.
Figure 7A:
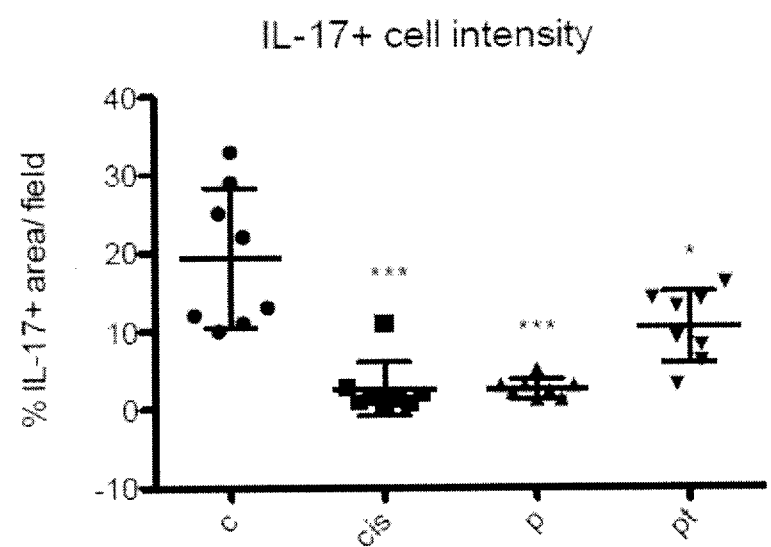
Figure 7B:
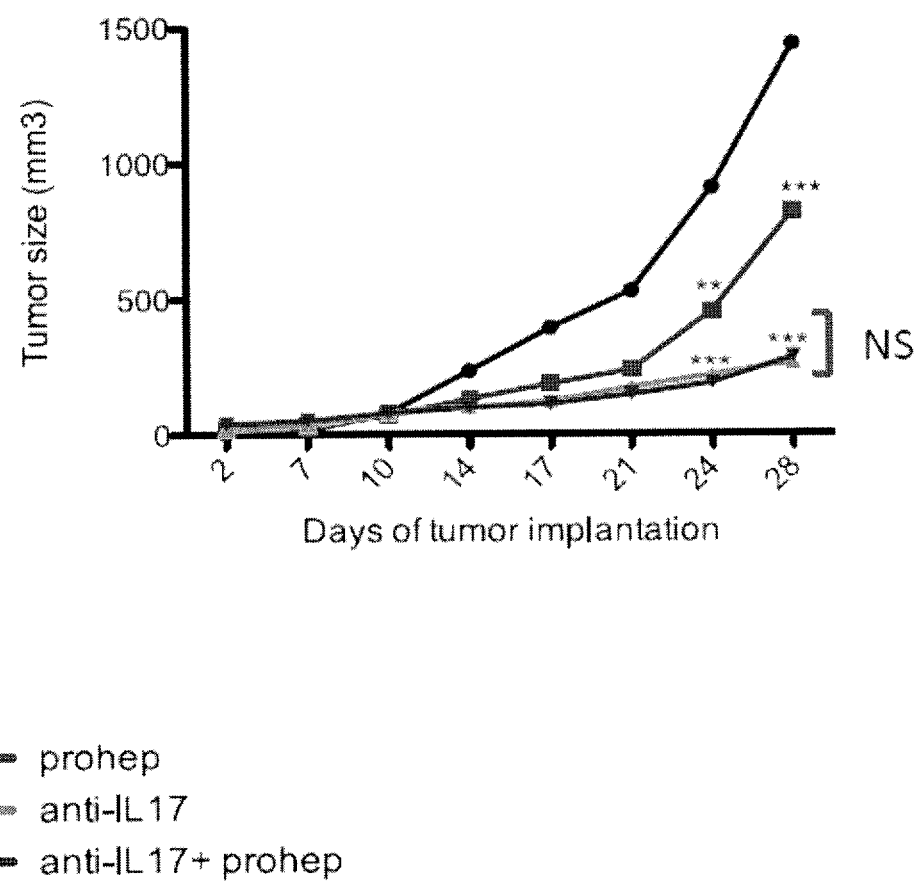
FIG. 7B shows tumor sizes over time in C57BL/6N mice inoculated with tumor and injected with anti-IL-17 antibody (200 µg/day) or control rat IgG. Tumor sizes were monitored for 1 month. Mice were under either a control or a ProHep diet starting from 1 week in advance of tumor inoculation.
Figure 7C:
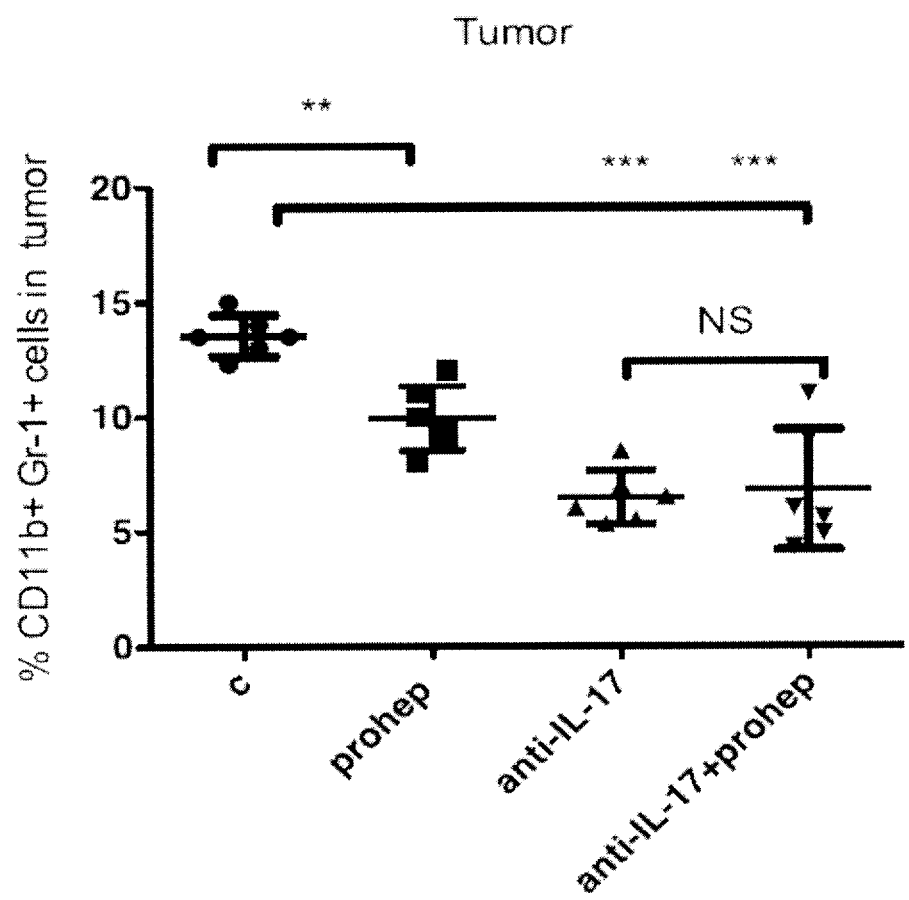
FIG. 7C shows flow cytometry analyses of % MDSC in tumor.

FIG. 7A shows immunostaining of IL-17 in representative tumor sections. Densities of IL-17+ cells were significantly smaller in ProHep groups. C57BL/6N mice were inoculated with tumor and injected with anti-IL-17 antibody (200 μg/day) or control rat IgG. Tumor sizes were monitored for 1 month. Mice were under either a control or a ProHep diet starting from 1 week in advance of tumor inoculation. As shown in FIG. 7B, ProHep failed to exhibit any effect on tumor progression after IL-17 neutralization. C) Flow cytometry analyses of % MDSC in tumor showed reduced infiltration of MDSC in ProHep and IL-17 neutralization (FIG. 7C).

Example 6—ProHep Prevents Tumor Outgrowth is Associated with Th17

Figure 8A:
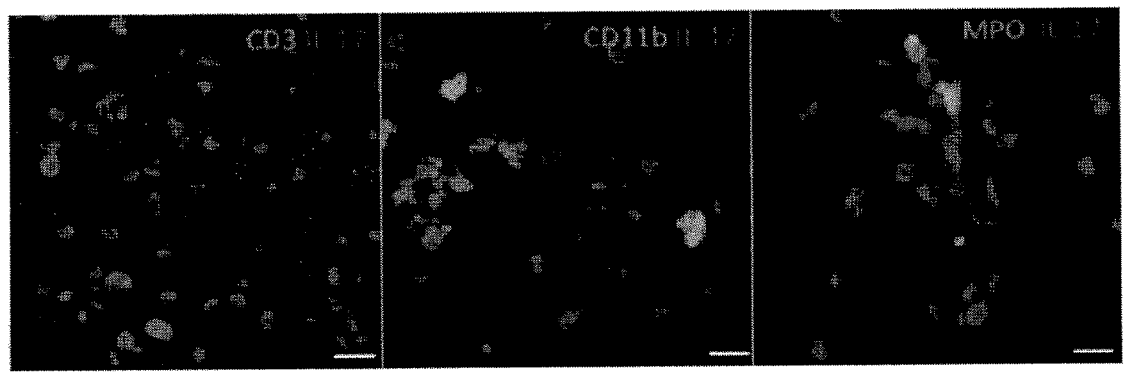
FIG. 8A shows confocal images of tumor sections with IL-17 staining (blue), co-stained (red) with CD3 (left panel), CD11b (middle panel) and MPO (right panel). Scale bar, 50 µm.
Figure 8A:
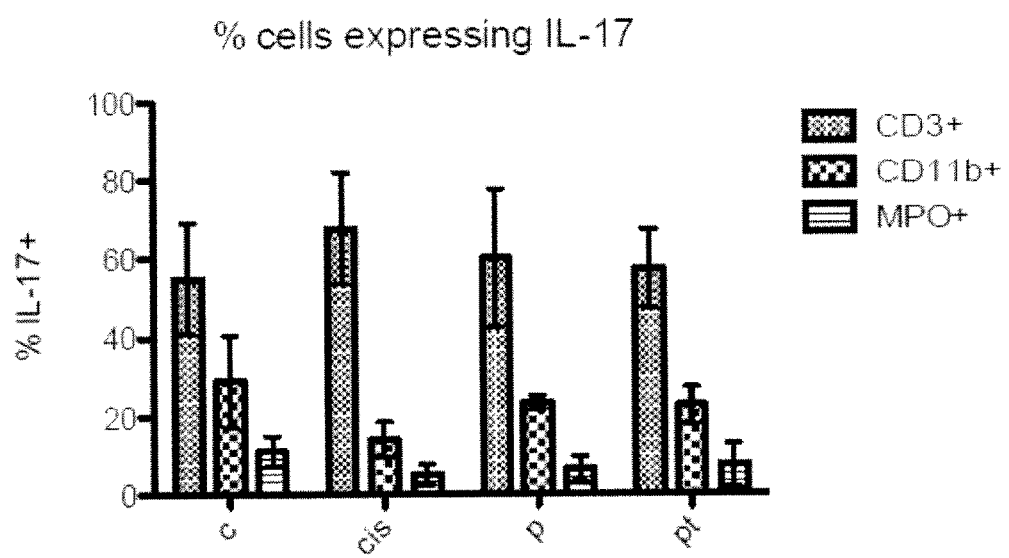
Figure 8B:
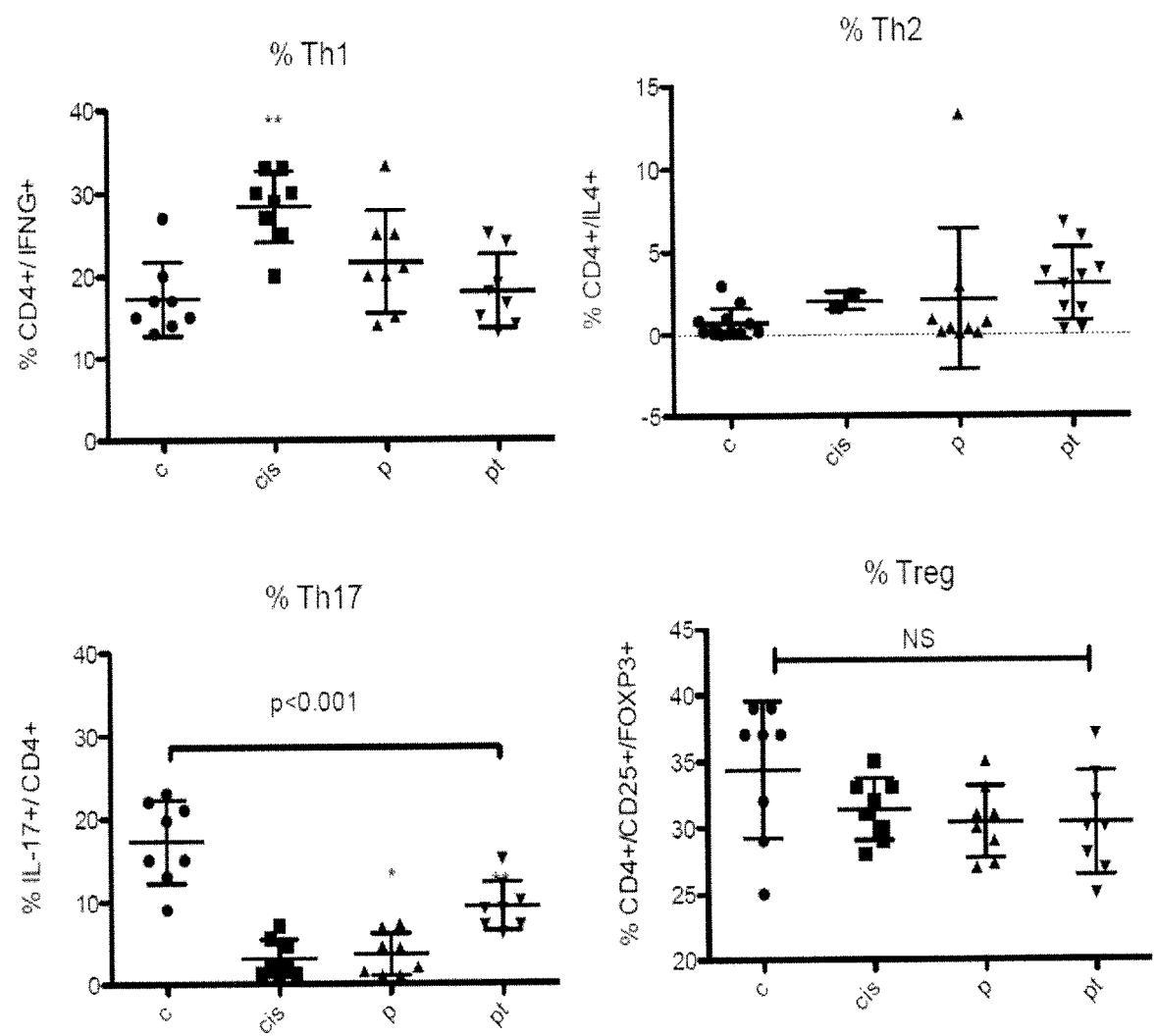
FIG. 8B shows flow cytometry analyses % Th subset in tumor.
Figure 8C:
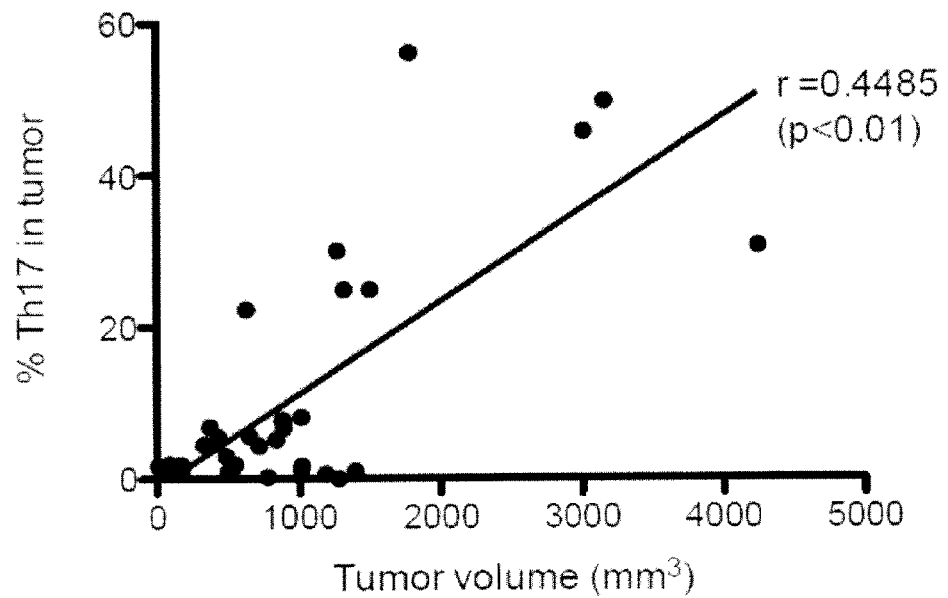
FIG. 8C shows correlation analysis of % Th17, MVD and tumor size.
Figure 8C:
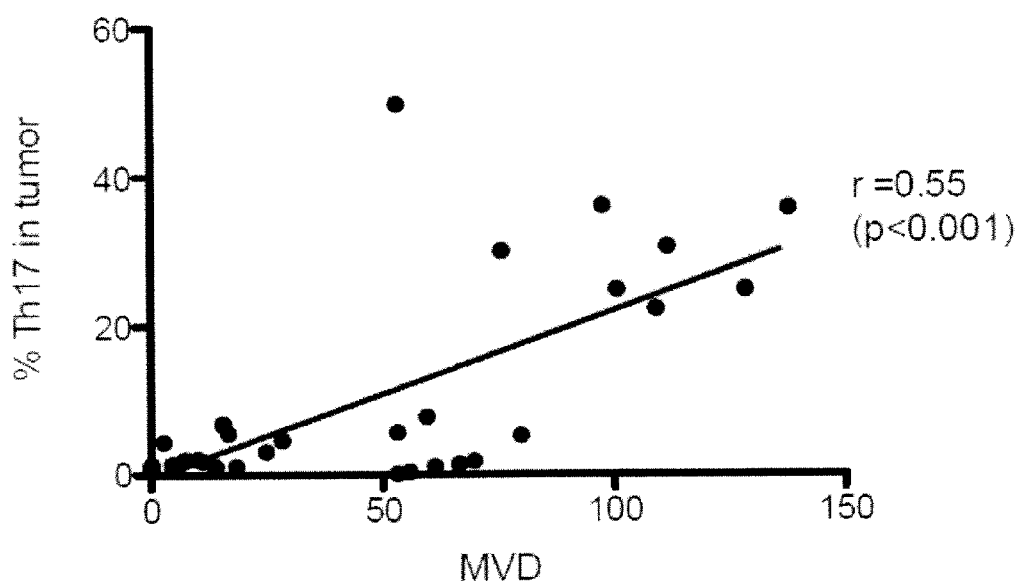
Figure 8D:
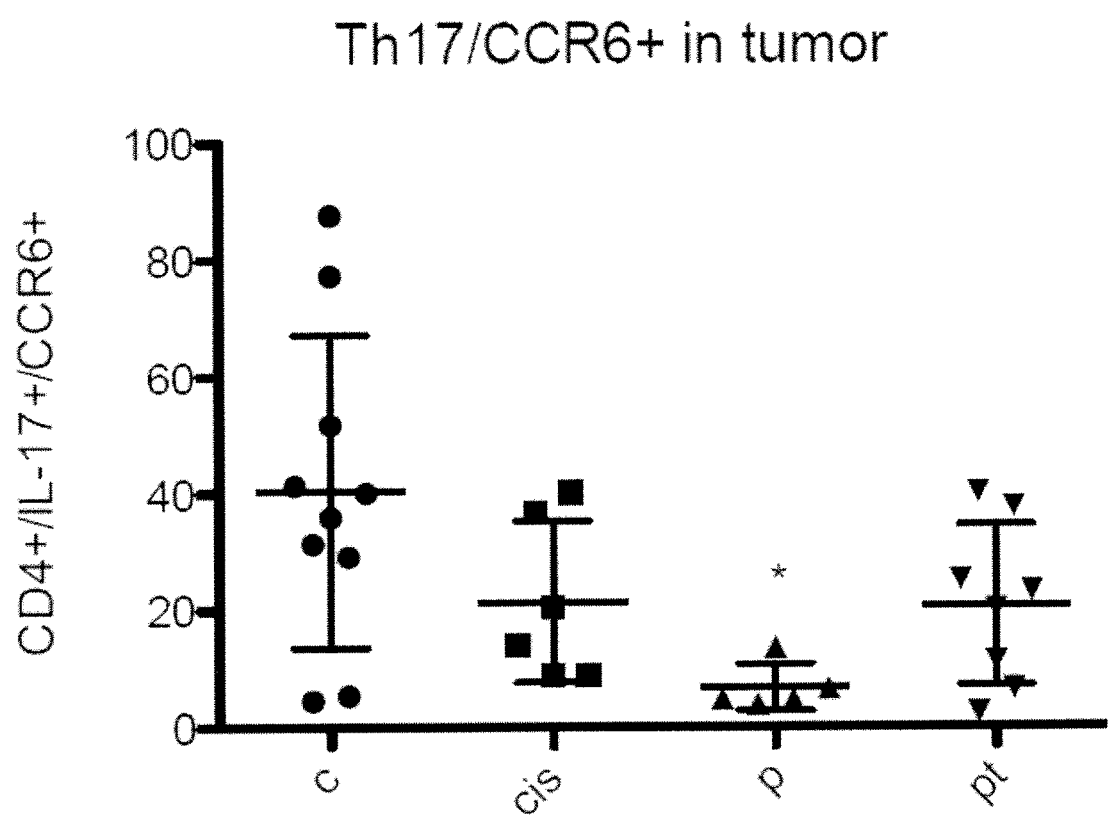
FIG. 8D shows phenotyping of Th17 in tumor.
Figure 8E:
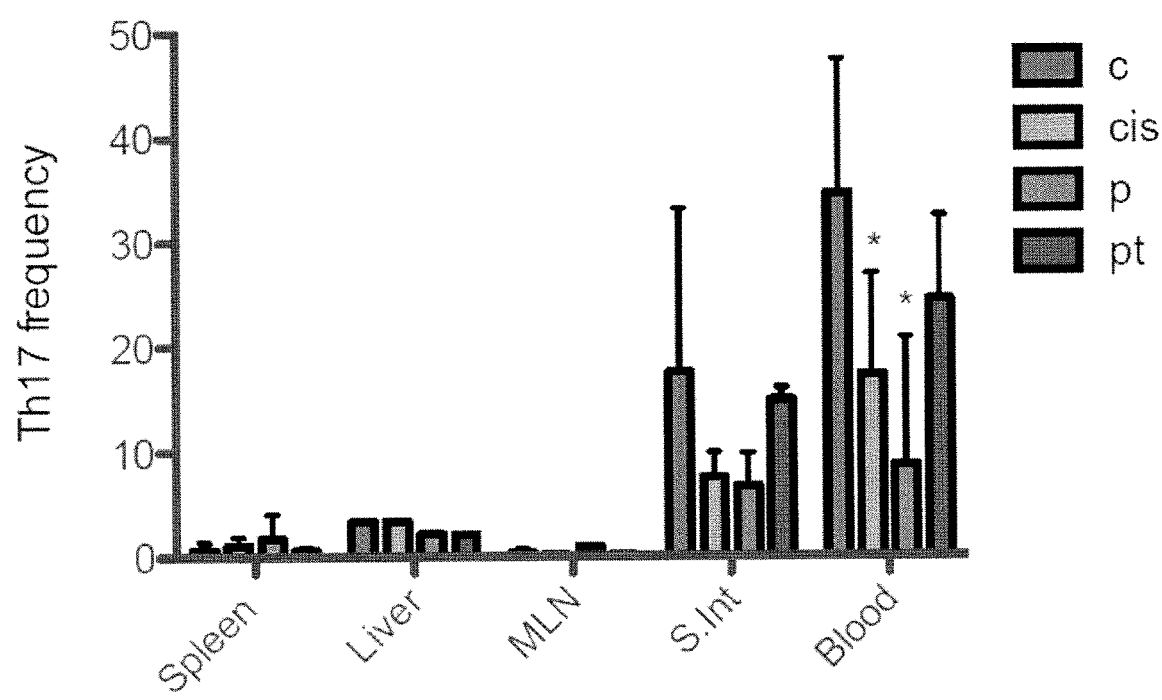
FIG. 8E shows Th17 frequency in various organs by flow cytometry.

FIG. 8A shows confocal images of tumor sections with IL-17 staining (blue), co-stained (red) with CD3 (left panel), CD11b (middle panel) and MPO (right panel). Scale bar, 50 μm. FIG. 8B shows flow cytometry analyses % Th subset in tumor. FIG. 8C shows the correlation analysis of % Th17, MVD and tumor size. FIG. 8D shows phenotyping of Th17 in tumor, and FIG. 8E shows the Th17 frequency in various organs by flow cytometry.

Immunostaining showed that the majority of IL-17+ cells in tumors were found to be CD3+ cells. Since Th cells were reported to be the major producer of IL-17, Th subset phenotyping was performed by flow cytometry and found that Th17 subset was significantly reduced in the tumor microenvironment, and their population were found to be correlated with reduced MVD and tumor size. Th17 in tumor has expressed migratory phenotype CCR6, suggesting these cells may be recruited from periphery site. Flow cytometry analyses showed a trend of reduced recruitment of Th17 from intestine to tumor via circulation.

Example 7—A ProHep Diet Reduces the Capacity of Naïve CD4+ T Cells to Differentiate into Th17

Figure 9A:
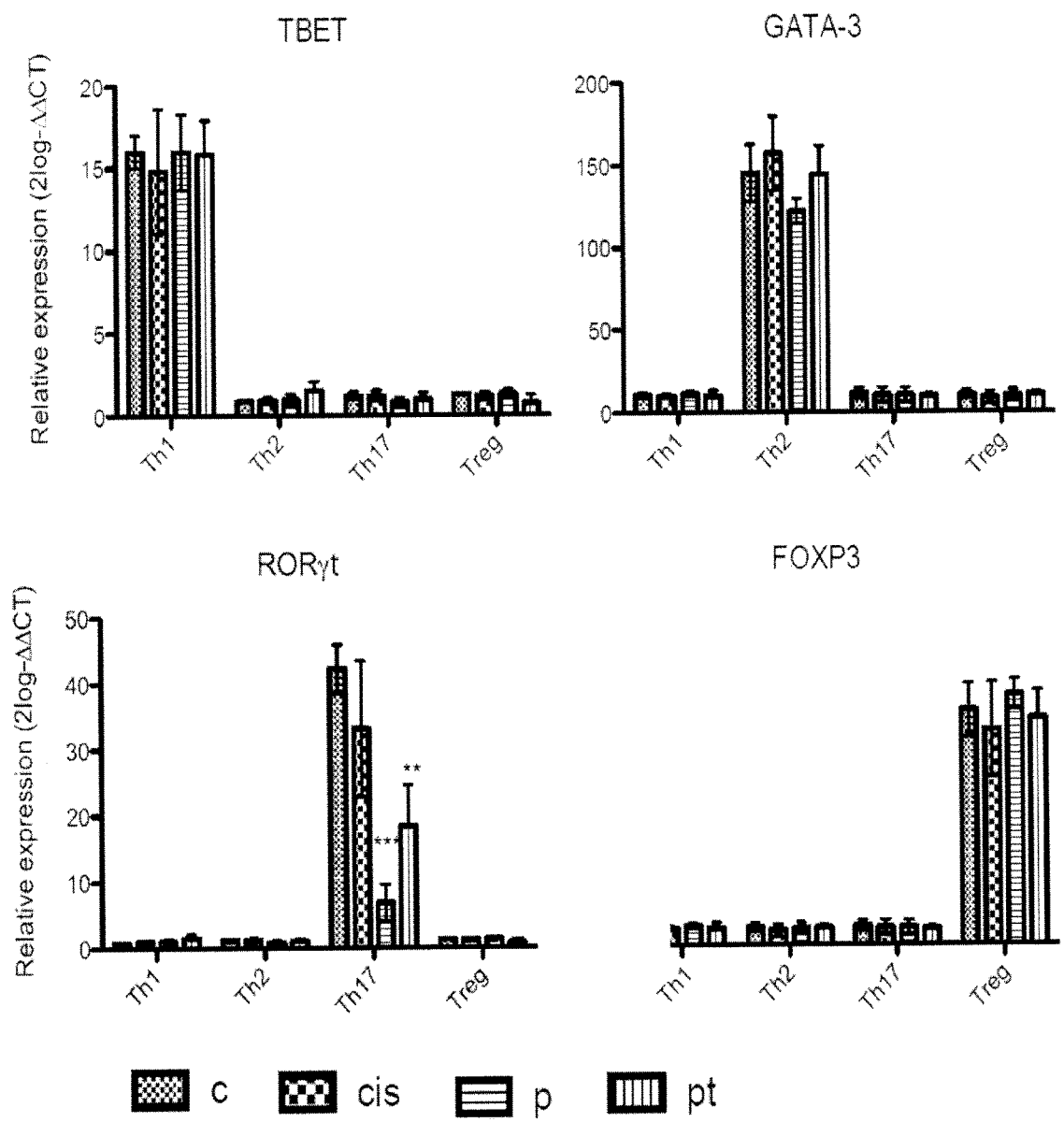
FIGS. 9A-9C show a ProHep diet reduces the capacity of naïve CD4+ T cells to differentiate into Th17. Naïve CD4+ CD62L+ T cells were isolated from mice gut under a control or a ProHep diet and differentiated into Th1, Th2, Th17 or Treg cells in the presence of anti-CD3 and anti-CD28 for 72 hours.
Figure 9B:
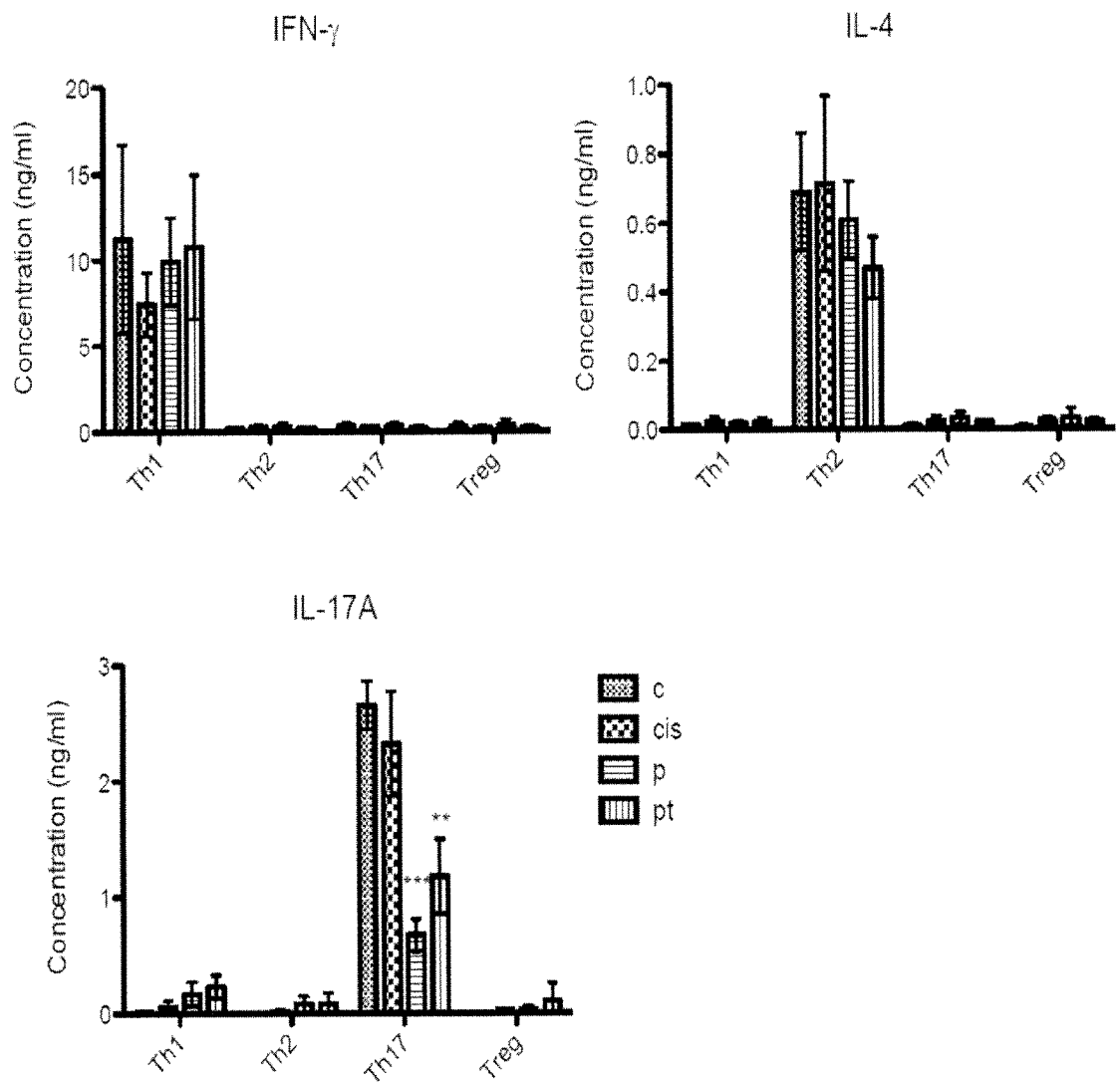
Figure 9C:
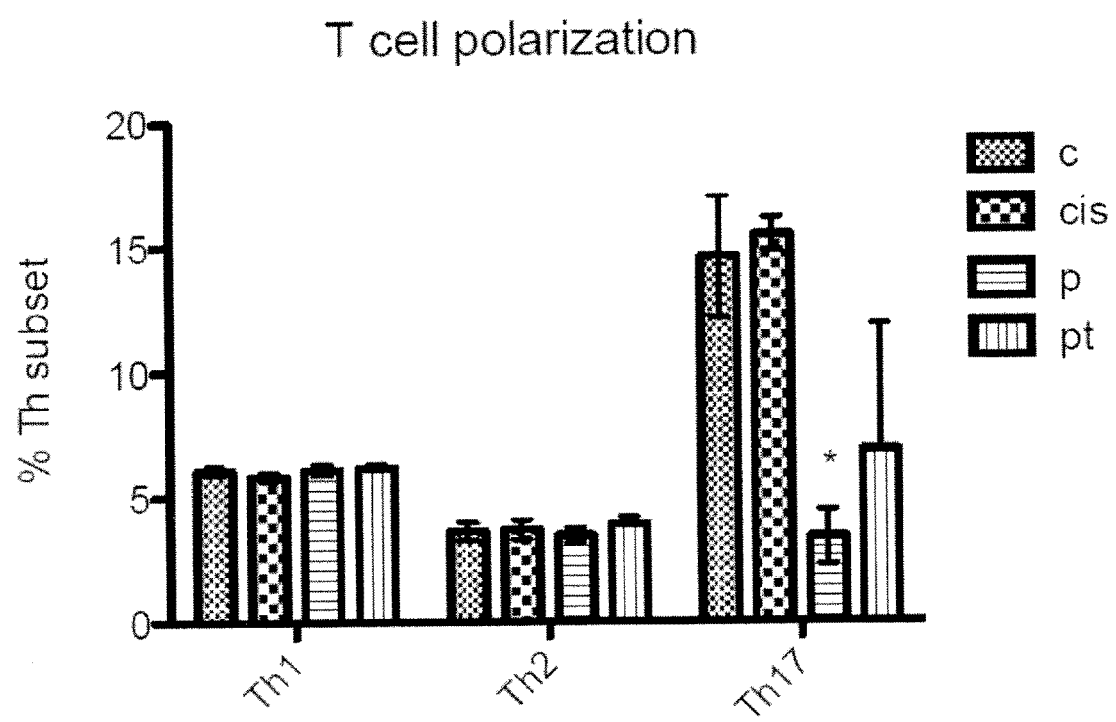

Naïve CD4+CD62L+ T cells were isolated from mouse gut under a control or a ProHep diet and differentiated into Th1, Th2, Th17 or Treg cells in the presence of anti-CD3 and anti-CD28 for 72 hours. FIG. 9A shows RT-qPCR analyses of Tbet, Gata3, Roryt and Foxp3 mRNA expression. Expression is presented relative to Gapdh expression. Significant downregulation of Th17 transcription factor Roryt was observed. FIG. 9B shows cytokine secretion measured by ELISA in supernatants of CD4+ T cells differentiated for 3 days. Production of IL-17 (right panel) was decreased while production of IFN-γ (left panel) and IL-4 (middle panel) from Th1 and Th2 was unaffected. FIG. 9C shows flow cytometry analyses of % Th1(CD4+IFN-γ+), Th2 (CD4+IL-4+) and Th17 (CD4+IL-17+) derived from naïve CD4+ T cells under polarizing conditions assessed for a 5 day culture. Representative data from three independent experiments are shown. Significant reduction of Th17 polarization was observed.

DISCUSSION

In this study, the use of probiotics in HCC treatment via immunomodulation in the tumor microenvironment is described. Probiotics are defined as live microorganisms that, when administered in adequate amounts, confer a health benefit on the host. Beneficial probiotic formulation (ProHep) comprising of (a) heat-inactivated *Lactobacillus rhamnosus* GG deposited under accession number ATCC 53103, also known as, *Lactobacillus acidophilus* (Moro) Hansen and Macquot, (b) viable *Escherichia coli* Nissle 1917, and (c) heat-inactivated VSL#3® was found to be effective to reduce subcutaneous HCC growth in mice when administered orally on daily basis for 38 days. Tumor size in the probiotic group was significantly smaller than control group starting from day 31, while the beneficial effect could be observed even earlier (day 28) when ProHep was administered 1 week before tumor inoculation. Yet, the anti-cancer effects of probiotic groups were less potent than drug (cisplatin) treatment group.

The smaller tumor size in the probiotic group was unlikely to be due to reduce cell proliferation but may be related to increase in necrotic cell death, as immunohistochemistry staining revealed that there were no significant differences in the number of Ki67+ cells in tumor tissue, while there was larger area of cell death (TO-PRO3) and no significant change in number of caspase 3+ apoptotic cells. Meanwhile, an increase in hypoxic (GLTU-1+) area was observed in the probiotic group, suggesting that increase in cell death was possibly related to increase hypoxia due to reduction in angiogenesis. Indeed, mean microvessel density, percentage area of blood vessel per tumor section and number of vessel sprouts, as quantified PECAM-1+ cells, were all significantly lower in tumors established in probiotic-treated mice as compared to control group. RT-qPCR analysis of tumor in the probiotic group has shown reduced expression of several angiogenic genes, including ANG2, FLT-1, KDR, TIE, TGFB, where their expression have been associated with reduced IL-17 and RORC expression by hierarchical gene clustering, suggesting that Th17 or IL-17 producing cells may be involved in the probiotics-mediated effect on HCC growth. This notion was further supported by the observation of reduced IL-17+ cells in tumor sections of the probiotic group, and that similar reduction of tumor growth could be observed in the probiotic group and control group after IL-17 antibody neutralization. Although several immune cells have been reported by these findings, most IL-17+ cells were co-stained with CD3, and the tumor infiltrating Th17 population has decreased in the probiotic group. Flow cytometic analysis that show reduced infiltration of angiogenic cells, such as myeloid derived suppressor cells, into the tumor microenvironment after IL-17 neutralization and probiotic treatment. Together these data suggest a role for probiotics in impairing tumor angiogenesis by modulating immune cell infiltration via Th17.

Since a majority of Th17 cells in the tumor microenvironment have an expressed migratory phenotype (CCR6+), it is possible that Th17 was recruited systemically into the tumor microenvironment. The gut seems to be the potential source of Th17, as a reduced Th17 population was found in the gut of the probiotic group by flow cytometry, but not in other organs such as spleen, mesenteric lymph node, blood, liver. Probiotics may reduce the ability of naïve T cells to differentiate into Th17 cells in the gut. Following activation of naïve T cells isolated from the gut of mice fed with probiotics, there was reduced gene expression of Rorc, the transcription factor of Th17, but not the transcription factor of TH1, TH2 and Treg. In addition, there was reduced IL-17A production from Th17 cells by ELISA, while IFN-γ or IL-4 secretion from TH1 and TH2 cells derived from mice under a probiotic diet were not affected. Intracellular staining analysis by flow cytometry also confirmed dampened IL-17A secretion from TH17 cells. Taken together, these results suggest that probiotics selectively affect TH17 cell differentiation in the gut and its recruitment into the tumor microenvironment.

In summary, our findings provide a method of reducing HCC growth with probiotic compositions via immunomodulation and open new avenues to the development of more effective cancer therapies.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It must be noted that as used herein and in the appended claims, the singular forms "a", "an", and "the" include plural reference unless the context clearly dictates otherwise. Thus, for example, reference to "a composition" includes a plurality of such compositions, reference to "the composition" is a reference to one or more compositions and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps. "Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other end-point, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different bacteria does not indicate that the listed bacteria are obvious one to the other, nor is it an admission of equivalence or obviousness.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of treating a subject at risk of or a subject diagnosed with hepatocellular carcinoma (HCC), the method comprising orally administering a probiotic composition comprising an effective amount of a combination of bacteria comprising (a) heat-inactivated *Lactobacillus rhamnosus* (GG) (deposited at the DSM under accession the ATCC 53103), (b) viable *Escherichia coli* Nissle 1917

(deposited at the DSM under accession number 6601), and (c) mixture of heat-inactivated bacteria of strains: *Bifidobacterium breve, Bifidobacterium longum, Bifidobacterium infantis, Lactobacillus acidophilus, Lactobacillus plantarum, Lactobacillus parcacasei, Lactobacillus bulgaricus, Streptococcus thermophiles*, wherein the effective amount of the combination of bacteria reduces the growth of hepatocellular carcinoma (HCC) in said subject.

2. The method of claim 1, wherein the probiotic composition is administered daily.

3. The method of claim 1, wherein the probiotic composition is administered daily for at least one month.

4. The method of claim 1, wherein the subject is diagnosed with HCC.

5. The method of claim 1, wherein the subject is at risk of HCC.

6. The method of claim 5, wherein the subject is diagnosed with hepatitis B virus, hepatitis C virus, or both.

7. The method of claim 5, wherein the subject has been exposed to aflatoxin B1 (AFB1).

8. The method of claim 5, wherein the subject is diagnosed with alcoholism.

9. The method of claim 1 further comprising, prior to administering the probiotic composition, diagnosing the subject as having HCC.

10. The method of claim 1 further comprising, prior to administering the probiotic composition, diagnosing the subject as at risk of HCC.

11. The method of claim 10, wherein diagnosing the subject as at risk of HCC comprises diagnosing the subject as having hepatitis B virus, hepatitis C virus, or both.

12. The method of claim 10, wherein diagnosing the subject as at risk of HCC comprises diagnosing the subject as having been exposed to aflatoxin B1 (AFB1).

13. The method of claim 10, wherein diagnosing the subject as at risk of HCC comprises diagnosing the subject as having alcoholism.

14. The method of claim 1, wherein the bacteria (a), (b), and (c) are each independently present in the probiotic composition at a concentration of about 20-55 weight percent.

* * * * *

UNITED STATES PATENT AND TRADEMARK OFFICE
CERTIFICATE OF CORRECTION

PATENT NO. : 10,016,468 B2
APPLICATION NO. : 14/460732
DATED : July 10, 2018
INVENTOR(S) : Hani El-Nezamy et al.

It is certified that error appears in the above-identified patent and that said Letters Patent is hereby corrected as shown below:

In the Specification

Column 6,
Line 19, "Roryt" should read --Rorγt--.

Column 18,
Line 16, "Roryt" should read --Rorγt--.

In the Claims

Column 20,
Line 66, "under accession the" should read --under the accession--.

Signed and Sealed this
Second Day of April, 2019

Andrei Iancu
*Director of the United States Patent and Trademark Office*